US012588957B2

(12) United States Patent
Bowling et al.

(10) Patent No.: US 12,588,957 B2
(45) Date of Patent: Mar. 31, 2026

(54) SURGICAL ROBOTIC SYSTEM WITH COMPLIANCE MECHANISM

(71) Applicant: MAKO Surgical Corp., Weston, FL (US)

(72) Inventors: David Gene Bowling, Los Ranchos De Albuquerque, NM (US); Ezra Johnson, Reeds Spring, MO (US)

(73) Assignee: MAKO Surgical Corp., Weston, FL (US)

( * ) Notice: Subject to any disclaimer, the term of this patent is extended or adjusted under 35 U.S.C. 154(b) by 372 days.

(21) Appl. No.: 18/204,552

(22) Filed: Jun. 1, 2023

(65) Prior Publication Data

US 2023/0390001 A1 Dec. 7, 2023

Related U.S. Application Data

(60) Provisional application No. 63/348,633, filed on Jun. 3, 2022.

(51) Int. Cl.
A61B 34/30 (2016.01)
A61B 34/00 (2016.01)
(Continued)

(52) U.S. Cl.
CPC .............. A61B 34/30 (2016.02); A61B 34/10 (2016.02); A61B 34/76 (2016.02);
(Continued)

(58) Field of Classification Search
CPC ... A61B 34/30; A61B 34/10; A61B 2034/107; A61B 34/20; A61B 2034/2055;
(Continued)

(56) References Cited

U.S. PATENT DOCUMENTS 4,124,026 A 11/1978 Berner et al.
4,359,906 A 11/1982 Cordey
(Continued)

FOREIGN PATENT DOCUMENTS

CN 201422918 Y 3/2010
CN 201542641 U 8/2010
(Continued)

OTHER PUBLICATIONS

International Search Report for Application No. PCT/US2023/024143 dated Aug. 28, 2023, 3 pages.
(Continued)

*Primary Examiner* — Jay Khandpur
(74) *Attorney, Agent, or Firm* — Howard & Howard Attorneys PLLC

(57) ABSTRACT

A surgical system includes a robotic manipulator and an end effector supported by the robotic manipulator. The end effector includes a surgical tool to interact with an anatomy and a compliance mechanism. The compliance mechanism enables the surgical tool to move relative to the robotic manipulator in response to external forces/torques applied to the surgical tool by the anatomy. The compliance mechanism has a stationary portion coupled to the robotic manipulator, a moveable portion coupled to the surgical tool, and a flexible portion disposed between the stationary portion and the moveable portion. An input device has a force/torque sensor that senses a force/torque applied to the input device by a user. The force/torque sensor is mechanically isolated from the external forces/torques applied to the surgical tool.

23 Claims, 7 Drawing Sheets

(51) Int. Cl.

| | |
|---|---|
| *A61B 34/10* | (2016.01) |
| *A61B 34/20* | (2016.01) |
| *A61B 34/37* | (2016.01) |
| *A61B 90/00* | (2016.01) |

(52) U.S. Cl.
CPC ......... *A61B 2034/107* (2016.02); *A61B 34/20* (2016.02); *A61B 2034/2055* (2016.02); *A61B 2034/306* (2016.02); *A61B 34/37* (2016.02); *A61B 2090/064* (2016.02)

(58) Field of Classification Search
CPC ... A61B 2034/306; A61B 34/37; A61B 34/76; A61B 2090/064
See application file for complete search history.

(56) References Cited

U.S. PATENT DOCUMENTS

| | | | |
|---|---|---|---|
| 4,922,436 | A | 5/1990 | Dohm et al. |
| 5,014,794 | A | 5/1991 | Hansson |
| 5,320,115 | A | 6/1994 | Kenna |
| 5,397,327 | A | 3/1995 | Koop et al. |
| 5,507,211 | A | 4/1996 | Wagner |
| 5,799,055 | A | 8/1998 | Peshkin et al. |
| 5,999,168 | A | 12/1999 | Rosenberg et al. |
| 6,154,201 | A | 11/2000 | Levin et al. |
| 6,228,089 | B1 | 5/2001 | Wahrburg |
| 6,236,875 | B1 | 5/2001 | Bucholz et al. |
| 6,246,200 | B1 | 6/2001 | Blumenkranz et al. |
| 6,271,828 | B1 | 8/2001 | Rosenberg et al. |
| 6,535,756 | B1 | 3/2003 | Simon et al. |
| 6,649,220 | B1 | 11/2003 | Krueger et al. |
| 6,680,595 | B2 | 1/2004 | Ito |
| 6,711,432 | B1 | 3/2004 | Krause et al. |
| 6,772,002 | B2 | 8/2004 | Schmidt et al. |
| 6,782,287 | B2 | 8/2004 | Grzeszczuk et al. |
| 6,785,572 | B2 | 8/2004 | Yanof et al. |
| 6,823,207 | B1 | 11/2004 | Jensen et al. |
| 6,837,892 | B2 | 1/2005 | Shoham |
| 6,866,671 | B2 | 3/2005 | Tierney et al. |
| 6,877,239 | B2 | 4/2005 | Leitner et al. |
| 6,920,347 | B2 | 7/2005 | Simon et al. |
| 6,947,786 | B2 | 9/2005 | Simon et al. |
| 6,993,374 | B2 | 1/2006 | Sasso |
| 7,001,393 | B2 | 2/2006 | Schwenke et al. |
| 7,048,745 | B2 | 5/2006 | Tierney et al. |
| 7,104,998 | B2 | 9/2006 | Yoon et al. |
| 7,107,883 | B2 | 9/2006 | Casutt |
| 7,188,626 | B2 | 3/2007 | Foley et al. |
| 7,194,120 | B2 | 3/2007 | Wicker et al. |
| 7,235,076 | B2 | 6/2007 | Pacheco |
| 7,294,106 | B2 | 11/2007 | Birkenbach et al. |
| 7,327,348 | B2 | 2/2008 | Goldenberg et al. |
| 7,331,965 | B2 | 2/2008 | Nielsen |
| 7,338,526 | B2 | 3/2008 | Steinberg |
| 7,396,357 | B2 | 7/2008 | Tornier et al. |
| 7,497,868 | B2 | 3/2009 | Steinberg |
| 7,542,791 | B2 | 6/2009 | Mire et al. |
| 7,567,833 | B2 | 7/2009 | Moctezuma De La Barrera et al. |
| 7,570,791 | B2 | 8/2009 | Frank et al. |
| 7,587,076 | B2 | 9/2009 | Kraus et al. |
| 7,587,235 | B2 | 9/2009 | Wist et al. |
| 7,607,238 | B2 | 10/2009 | Kim et al. |
| 7,630,753 | B2 | 12/2009 | Simon et al. |
| 7,637,913 | B2 | 12/2009 | De Villiers et al. |
| 7,637,929 | B2 | 12/2009 | Auth |
| 7,670,343 | B2 | 3/2010 | Meridew et al. |
| 7,677,801 | B2 | 3/2010 | Pakzaban |
| 7,699,877 | B2 | 4/2010 | Davison |
| 7,722,530 | B2 | 5/2010 | Davison |
| 7,725,162 | B2 | 5/2010 | Malackowski et al. |
| 7,736,630 | B2 | 6/2010 | Touitou et al. |
| 7,747,312 | B2 | 6/2010 | Barrick et al. |
| 7,751,868 | B2 | 7/2010 | Glossop |
| 7,766,930 | B2 | 8/2010 | DiPoto et al. |
| 7,799,036 | B2 | 9/2010 | Davison et al. |
| 7,822,244 | B2 | 10/2010 | Blumhofer |
| 7,831,292 | B2 | 11/2010 | Quaid et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,843,158 | B2 | 11/2010 | Prisco |
| 7,853,305 | B2 | 12/2010 | Simon et al. |
| 7,887,567 | B2 | 2/2011 | Shoham et al. |
| 7,900,524 | B2 | 3/2011 | Calloway et al. |
| 8,010,177 | B2 | 8/2011 | Csavoy et al. |
| 8,010,180 | B2 | 8/2011 | Quaid et al. |
| 8,010,181 | B2 | 8/2011 | Smith et al. |
| 8,016,835 | B2 | 9/2011 | Birkmeyer et al. |
| 8,036,441 | B2 | 10/2011 | Frank et al. |
| 8,046,054 | B2 | 10/2011 | Kim et al. |
| 8,052,688 | B2 | 11/2011 | Wolf, II |
| 8,057,407 | B2 | 11/2011 | Martinelli et al. |
| 8,092,471 | B2 | 1/2012 | Momoi et al. |
| 8,100,950 | B2 | 1/2012 | St. Clair et al. |
| 8,108,025 | B2 | 1/2012 | Csavoy et al. |
| 8,116,848 | B2 | 2/2012 | Shahidi |
| 8,133,234 | B2 | 3/2012 | Meridew et al. |
| 8,165,660 | B2 | 4/2012 | Pfister et al. |
| 8,167,823 | B2 | 5/2012 | Nycz et al. |
| 8,182,469 | B2 | 5/2012 | Anderson et al. |
| 8,182,470 | B2 | 5/2012 | Devengenzo et al. |
| 8,182,491 | B2 | 5/2012 | Selover et al. |
| 8,195,272 | B2 | 6/2012 | Piferi et al. |
| 8,202,244 | B2 | 6/2012 | Cohen et al. |
| 8,206,405 | B2 | 6/2012 | Beverland et al. |
| 8,219,177 | B2 | 7/2012 | Smith et al. |
| 8,219,178 | B2 | 7/2012 | Smith et al. |
| 8,241,296 | B2 | 8/2012 | Wasielewski |
| 8,265,731 | B2 | 9/2012 | Kukuk et al. |
| 8,271,066 | B2 | 9/2012 | Sarin et al. |
| 8,277,491 | B2 | 10/2012 | Selover et al. |
| 8,286,723 | B2 | 10/2012 | Puzio et al. |
| 8,311,611 | B2 | 11/2012 | Csavoy et al. |
| 8,328,852 | B2 | 12/2012 | Zehavi et al. |
| 8,335,553 | B2 | 12/2012 | Rubner et al. |
| 8,337,426 | B2 | 12/2012 | Nycz |
| 8,374,678 | B2 | 2/2013 | Graumann |
| 8,394,144 | B2 | 3/2013 | Zehavi et al. |
| 8,395,342 | B2 | 3/2013 | Prisco |
| 8,419,717 | B2 | 4/2013 | Diolaiti et al. |
| 8,425,522 | B2 | 4/2013 | Bonutti |
| 8,442,677 | B2 | 5/2013 | Shoham |
| 8,454,583 | B2 | 6/2013 | Perez-Cruet et al. |
| 8,454,619 | B1 | 6/2013 | Head |
| 8,469,963 | B2 | 6/2013 | Shoham |
| 8,491,603 | B2 | 7/2013 | Yeung et al. |
| 8,500,738 | B2 | 8/2013 | Wolf, II |
| 8,509,503 | B2 | 8/2013 | Nahum et al. |
| 8,518,051 | B2 | 8/2013 | Shoham et al. |
| 8,571,638 | B2 | 10/2013 | Shoham |
| 8,572,860 | B2 | 11/2013 | Fritzinger |
| 8,615,288 | B2 | 12/2013 | Govari et al. |
| 8,620,473 | B2 | 12/2013 | Diolaiti et al. |
| 8,634,897 | B2 | 1/2014 | Simon et al. |
| 8,644,906 | B2 | 2/2014 | Piferi et al. |
| 8,657,829 | B2 | 2/2014 | McCardel |
| 8,705,829 | B2 | 4/2014 | Frank et al. |
| 8,706,185 | B2 | 4/2014 | Foley et al. |
| 8,709,016 | B2 | 4/2014 | Park et al. |
| 8,740,885 | B2 | 6/2014 | Larkin et al. |
| 8,747,476 | B2 | 6/2014 | Steinberg |
| 8,758,413 | B2 | 6/2014 | Heiges et al. |
| 8,814,877 | B2 | 8/2014 | Wasielewski |
| 8,814,914 | B2 | 8/2014 | Miller et al. |
| 8,838,205 | B2 | 9/2014 | Shoham et al. |
| 8,840,629 | B2 | 9/2014 | Bonutti |
| 8,848,977 | B2 | 9/2014 | Bammer et al. |
| 8,864,752 | B2 | 10/2014 | Diolaiti et al. |
| 8,876,837 | B2 | 11/2014 | Smith et al. |
| 8,900,244 | B2 | 12/2014 | Meridew et al. |
| 8,911,429 | B2 | 12/2014 | Olds et al. |
| 8,951,256 | B2 | 2/2015 | Burroughs |
| 8,961,526 | B2 | 2/2015 | Burroughs |

(56) References Cited

U.S. PATENT DOCUMENTS

| | | | |
|---|---|---|---|
| 8,974,460 | B2 | 3/2015 | De la Fuente Klein et al. |
| 8,979,859 | B2 | 3/2015 | Leparmentier et al. |
| 8,992,580 | B2 | 3/2015 | Bar et al. |
| 8,998,909 | B2 | 4/2015 | Gillman et al. |
| 9,008,757 | B2 | 4/2015 | Wu |
| 9,011,456 | B2 | 4/2015 | Ranawat et al. |
| 9,017,313 | B2 | 4/2015 | Steinberg |
| 9,042,960 | B2 | 5/2015 | Neubardt |
| 9,044,190 | B2 | 6/2015 | Rubner et al. |
| 9,050,108 | B2 | 6/2015 | Grinberg et al. |
| 9,056,015 | B2 | 6/2015 | Zehavi et al. |
| 9,066,751 | B2 | 6/2015 | Sasso |
| 9,066,755 | B1 | 6/2015 | Jacobs et al. |
| 9,078,685 | B2 | 7/2015 | Smith et al. |
| 9,101,443 | B2 | 8/2015 | Bonutti |
| 9,107,721 | B2 | 8/2015 | Plotkin |
| 9,119,572 | B2 | 9/2015 | Gorek et al. |
| 9,119,655 | B2 | 9/2015 | Bowling et al. |
| 9,125,556 | B2 | 9/2015 | Zehavi et al. |
| 9,125,680 | B2 | 9/2015 | Kostrzewski et al. |
| 9,131,986 | B2 | 9/2015 | Greer et al. |
| 9,138,319 | B2 | 9/2015 | Fanson et al. |
| 9,149,281 | B2 | 10/2015 | Bonutti |
| 9,155,544 | B2 | 10/2015 | Bonutti |
| 9,161,799 | B2 | 10/2015 | Benson et al. |
| 9,168,154 | B2 | 10/2015 | Behzadi |
| 9,192,395 | B2 | 11/2015 | Bonutti |
| 9,198,714 | B2 | 12/2015 | Worrell et al. |
| 9,198,731 | B2 | 12/2015 | Balaji et al. |
| 9,211,128 | B2 | 12/2015 | Gillman et al. |
| 9,211,160 | B2 | 12/2015 | Pivotto et al. |
| 9,220,612 | B2 | 12/2015 | Behzadi |
| 9,232,906 | B2 | 1/2016 | Wolf, II |
| 9,237,861 | B2 | 1/2016 | Nahum et al. |
| 9,240,046 | B2 | 1/2016 | Carrell et al. |
| 9,241,771 | B2 | 1/2016 | Kostrzewski et al. |
| 9,243,881 | B2 | 1/2016 | Bourque et al. |
| 9,265,551 | B2 | 2/2016 | Kust et al. |
| 9,271,741 | B2 | 3/2016 | Bonutti |
| 9,271,779 | B2 | 3/2016 | Bonutti |
| 9,283,048 | B2 | 3/2016 | Kostrzewski et al. |
| 9,295,500 | B2 | 3/2016 | Marigowda |
| 9,308,050 | B2 | 4/2016 | Kostrzewski et al. |
| 9,333,042 | B2 | 5/2016 | Diolaiti et al. |
| 9,339,278 | B2 | 5/2016 | Meridew et al. |
| 9,339,345 | B2 | 5/2016 | Song et al. |
| 9,345,387 | B2 | 5/2016 | Larkin |
| 9,358,130 | B2 | 6/2016 | Livorsi et al. |
| 9,398,962 | B2 | 7/2016 | Steinberg |
| 9,439,675 | B2 | 9/2016 | Penenberg |
| 9,452,019 | B2 | 9/2016 | Schena et al. |
| 9,456,827 | B2 | 10/2016 | Grinberg et al. |
| 9,462,943 | B2 | 10/2016 | Brownell |
| 9,468,538 | B2 | 10/2016 | Nycz et al. |
| 9,480,516 | B2 | 11/2016 | Crawford et al. |
| 9,486,227 | B2 | 11/2016 | Bonutti |
| 9,491,415 | B2 | 11/2016 | Deitz et al. |
| 9,492,241 | B2 | 11/2016 | Joskowicz et al. |
| 9,513,176 | B1 | 12/2016 | Weber et al. |
| 9,519,341 | B2 | 12/2016 | Hasegawa et al. |
| 9,532,730 | B2 | 1/2017 | Wasielewski |
| 9,532,849 | B2 | 1/2017 | Anderson et al. |
| 9,536,309 | B2 | 1/2017 | Sela et al. |
| 9,539,112 | B2 | 1/2017 | Thornberry |
| 9,545,233 | B2 | 1/2017 | Sirpad et al. |
| 9,545,280 | B2 | 1/2017 | Crawford et al. |
| 9,549,781 | B2 | 1/2017 | He et al. |
| 9,554,763 | B2 | 1/2017 | Daon et al. |
| 9,554,864 | B2 | 1/2017 | Taylor et al. |
| 9,554,865 | B2 | 1/2017 | Olds et al. |
| 9,561,082 | B2 | 2/2017 | Yen et al. |
| 9,566,122 | B2 | 2/2017 | Bowling et al. |
| 9,576,353 | B2 | 2/2017 | Mahn et al. |
| 9,585,677 | B2 | 3/2017 | Garcia et al. |
| 9,585,725 | B2 | 3/2017 | Bonutti |
| 9,585,768 | B2 | 3/2017 | Sherman et al. |
| 9,592,096 | B2 | 3/2017 | Maillet et al. |
| 9,600,138 | B2 | 3/2017 | Thomas et al. |
| 9,603,665 | B2 | 3/2017 | Bowling et al. |
| 9,622,757 | B2 | 4/2017 | Bourque et al. |
| 9,622,779 | B2 | 4/2017 | Horton et al. |
| 9,629,687 | B2 | 4/2017 | Bonutti |
| 9,636,162 | B2 | 5/2017 | Crawford et al. |
| 9,649,096 | B2 | 5/2017 | Sholev |
| 9,649,160 | B2 | 5/2017 | van der Walt et al. |
| 9,649,202 | B2 | 5/2017 | Behzadi et al. |
| 9,655,649 | B2 | 5/2017 | Shoham |
| 9,662,160 | B2 | 5/2017 | Beale et al. |
| 9,662,174 | B2 | 5/2017 | Taylor et al. |
| 9,668,768 | B2 | 6/2017 | Piron et al. |
| 9,668,875 | B2 | 6/2017 | Steinberg |
| 9,675,272 | B2 | 6/2017 | Selover et al. |
| 9,687,306 | B2 | 6/2017 | Markey et al. |
| 9,693,878 | B2 | 7/2017 | Kunz et al. |
| 9,707,043 | B2 | 7/2017 | Bozung |
| 9,713,499 | B2 | 7/2017 | Bar et al. |
| 9,724,167 | B2 | 8/2017 | Ziaei et al. |
| 9,734,632 | B2 | 8/2017 | Thomas et al. |
| 9,737,326 | B2 | 8/2017 | Worrell et al. |
| 9,743,971 | B2 | 8/2017 | Belkoff et al. |
| 9,743,995 | B2 | 8/2017 | Lohmeier et al. |
| 9,750,510 | B2 | 9/2017 | Kostrzewski et al. |
| 9,750,545 | B2 | 9/2017 | Cryder et al. |
| 9,757,087 | B2 | 9/2017 | Simon et al. |
| 9,782,229 | B2 | 10/2017 | Crawford et al. |
| 9,788,966 | B2 | 10/2017 | Steinberg |
| 9,795,319 | B2 | 10/2017 | Lavallee et al. |
| 9,795,394 | B2 | 10/2017 | Bonutti |
| 9,808,318 | B2 | 11/2017 | Bonutti |
| 9,811,066 | B1 | 11/2017 | Linnell |
| 9,814,535 | B2 | 11/2017 | Bar et al. |
| 9,815,206 | B2 | 11/2017 | Balicki et al. |
| 9,833,292 | B2 | 12/2017 | Kostrzewski et al. |
| 9,833,907 | B1 | 12/2017 | Linnell et al. |
| 9,862,099 | B1 | 1/2018 | Linnell et al. |
| 9,877,793 | B2 | 1/2018 | Bonutti |
| 9,931,059 | B2 | 4/2018 | Borja |
| 9,987,092 | B2 | 6/2018 | Hladio et al. |
| 9,987,753 | B1 | 6/2018 | Linnell et al. |
| 9,993,309 | B2 | 6/2018 | Bowling |
| 10,004,562 | B2 | 6/2018 | Kostrzewski et al. |
| RE46,954 | E | 7/2018 | Pedicini |
| 10,028,722 | B2 | 7/2018 | Moreau-Gaudry et al. |
| 10,028,800 | B2 | 7/2018 | Bourque et al. |
| 10,034,753 | B2 | 7/2018 | Dressler et al. |
| 10,039,605 | B2 | 8/2018 | Kostrzewski et al. |
| 10,052,761 | B2 | 8/2018 | Langenfeld |
| 10,076,385 | B2 | 9/2018 | Shoham et al. |
| 10,080,509 | B2 | 9/2018 | Wasielewski |
| 10,080,615 | B2 | 9/2018 | Bartelme et al. |
| 10,085,786 | B2 | 10/2018 | Chandanson et al. |
| 10,172,679 | B2 | 1/2019 | Mewes et al. |
| 10,191,560 | B2 | 1/2019 | Linnell |
| 10,201,391 | B2 | 2/2019 | Bonutti |
| 10,201,903 | B1 | 2/2019 | Linnell et al. |
| 10,206,731 | B2 | 2/2019 | Kust et al. |
| 10,226,298 | B2 | 3/2019 | Ourselin et al. |
| 10,251,719 | B2 | 4/2019 | Mahdi |
| 10,259,122 | B2 | 4/2019 | Odhner et al. |
| 10,265,128 | B2 | 4/2019 | Bonutti |
| 10,335,183 | B2 | 7/2019 | Worrell et al. |
| 10,383,674 | B2 | 8/2019 | Sexson et al. |
| 10,413,371 | B2 | 9/2019 | Sweeney, II et al. |
| 10,531,926 | B2 | 1/2020 | Roessler |
| 10,611,030 | B2 | 4/2020 | Stone et al. |
| 10,814,407 | B2 | 10/2020 | Sweet et al. |
| 11,033,341 | B2 | 6/2021 | Kang et al. |
| 11,065,069 | B2 | 7/2021 | Kang et al. |
| 11,160,620 | B2 | 11/2021 | Ebbitt et al. |
| 11,219,487 | B2 | 1/2022 | He et al. |
| 11,291,507 | B2 | 4/2022 | Stawiaski et al. |
| 2003/0173096 | A1 | 9/2003 | Setton et al. |
| 2003/0181800 | A1 | 9/2003 | Bonutti |
| 2005/0085717 | A1 | 4/2005 | Shahidi |

(56) References Cited

U.S. PATENT DOCUMENTS

| | | |
|---|---|---|
| 2005/0149050 A1 | 7/2005 | Stifter et al. |
| 2005/0171557 A1 | 8/2005 | Shoham |
| 2006/0036264 A1 | 2/2006 | Selover et al. |
| 2006/0142657 A1 | 6/2006 | Quaid et al. |
| 2007/0058406 A1 | 3/2007 | Inoshita et al. |
| 2007/0093689 A1 | 4/2007 | Steinberg |
| 2007/0156157 A1 | 7/2007 | Nahum et al. |
| 2007/0250078 A1 | 10/2007 | Stuart |
| 2008/0004634 A1 | 1/2008 | Farritor et al. |
| 2008/0058837 A1 | 3/2008 | Steinberg |
| 2008/0071374 A1 | 3/2008 | Steinberg |
| 2008/0108994 A1 | 5/2008 | Steinberg |
| 2008/0114376 A1 | 5/2008 | Steinberg |
| 2008/0147188 A1 | 6/2008 | Steinberg |
| 2008/0249536 A1 | 10/2008 | Stahler et al. |
| 2008/0275367 A1 | 11/2008 | Barbagli et al. |
| 2008/0281332 A1 | 11/2008 | Taylor |
| 2009/0182348 A1 | 7/2009 | Nahapetian et al. |
| 2010/0009825 A1 | 1/2010 | Norton et al. |
| 2010/0137871 A1 | 6/2010 | Borja |
| 2010/0204714 A1 | 8/2010 | Shoham |
| 2010/0241129 A1 | 9/2010 | Markey et al. |
| 2011/0015649 A1 | 1/2011 | Anvari et al. |
| 2011/0066160 A1 | 3/2011 | Simaan et al. |
| 2011/0092859 A1 | 4/2011 | Neubardt |
| 2011/0184390 A1 | 7/2011 | Zanni et al. |
| 2011/0210229 A1 | 9/2011 | Bonnet et al. |
| 2011/0306873 A1 | 12/2011 | Shenai et al. |
| 2012/0046665 A1 | 2/2012 | Kim |
| 2012/0071863 A1 | 3/2012 | Lee et al. |
| 2012/0143211 A1 | 6/2012 | Kishi |
| 2012/0209117 A1 | 8/2012 | Mozes et al. |
| 2012/0283747 A1 | 11/2012 | Popovic |
| 2012/0330429 A1 | 12/2012 | Axelson, Jr. et al. |
| 2013/0307955 A1 | 11/2013 | Deitz et al. |
| 2013/0345718 A1 | 12/2013 | Crawford et al. |
| 2014/0031722 A1 | 1/2014 | Li et al. |
| 2014/0052150 A1 | 2/2014 | Taylor et al. |
| 2014/0058406 A1 | 2/2014 | Tsekos |
| 2014/0112344 A1 | 4/2014 | Mineshita |
| 2014/0135791 A1 | 5/2014 | Nikou et al. |
| 2014/0135796 A1 | 5/2014 | Simon et al. |
| 2014/0180290 A1 | 6/2014 | Otto et al. |
| 2014/0197844 A1 | 7/2014 | Chang |
| 2014/0222012 A1 | 8/2014 | Belkoff et al. |
| 2014/0257296 A1 | 9/2014 | Morgenstern Lopez |
| 2014/0275955 A1 | 9/2014 | Crawford et al. |
| 2014/0276949 A1 | 9/2014 | Staunton et al. |
| 2014/0309560 A1 | 10/2014 | Bonutti |
| 2014/0316436 A1 | 10/2014 | Bar et al. |
| 2014/0360305 A1 | 12/2014 | Olds et al. |
| 2014/0371577 A1 | 12/2014 | Maillet et al. |
| 2014/0378999 A1 | 12/2014 | Crawford et al. |
| 2015/0031985 A1 | 1/2015 | Reddy et al. |
| 2015/0032164 A1 | 1/2015 | Crawford et al. |
| 2015/0100066 A1 | 4/2015 | Kostrzewski et al. |
| 2015/0112344 A1 | 4/2015 | Shoham et al. |
| 2015/0142372 A1 | 5/2015 | Singh |
| 2015/0182285 A1 | 7/2015 | Yen et al. |
| 2015/0196326 A1 | 7/2015 | Bar et al. |
| 2015/0196365 A1 | 7/2015 | Kostrzewski et al. |
| 2015/0202009 A1 | 7/2015 | Nussbaumer et al. |
| 2015/0209056 A1 | 7/2015 | Shoham et al. |
| 2015/0209119 A1 | 7/2015 | Theodore et al. |
| 2015/0223897 A1 | 8/2015 | Kostrzewski et al. |
| 2015/0223906 A1 | 8/2015 | O'Neill et al. |
| 2015/0238206 A1 | 8/2015 | Benson et al. |
| 2015/0272696 A1 | 10/2015 | Fry et al. |
| 2015/0289992 A1 | 10/2015 | Anglin et al. |
| 2015/0305817 A1 | 10/2015 | Kostrzewski |
| 2015/0313684 A1 | 11/2015 | Fanson et al. |
| 2015/0327948 A1 | 11/2015 | Schoepp et al. |
| 2015/0335386 A1 | 11/2015 | Smith et al. |
| 2015/0351860 A1 | 12/2015 | Piron et al. |
| 2015/0366624 A1 | 12/2015 | Kostrzewski et al. |
| 2016/0000512 A1 | 1/2016 | Gombert et al. |
| 2016/0008011 A1 | 1/2016 | Kostrzewski |
| 2016/0030117 A1 | 2/2016 | Mewes |
| 2016/0038238 A1 | 2/2016 | Kostrzewski et al. |
| 2016/0038242 A1 | 2/2016 | Lo Iacono et al. |
| 2016/0081753 A1 | 3/2016 | Kostrzewski |
| 2016/0081754 A1 | 3/2016 | Kostrzewski et al. |
| 2016/0081819 A1 | 3/2016 | Kelman et al. |
| 2016/0095631 A1 | 4/2016 | Stad |
| 2016/0095720 A1 | 4/2016 | Behzadi |
| 2016/0120612 A1 | 5/2016 | Yorimoto |
| 2016/0128789 A1 | 5/2016 | Kostrzewski et al. |
| 2016/0151120 A1 | 6/2016 | Kostrzewski et al. |
| 2016/0157941 A1 | 6/2016 | Anvari et al. |
| 2016/0175110 A1 | 6/2016 | Behzadi et al. |
| 2016/0199141 A1 | 7/2016 | Mewes et al. |
| 2016/0202134 A1* | 7/2016 | Malackowski ........ B25J 9/1633 |
| | | 73/862.05 |
| 2016/0206347 A1 | 7/2016 | Bar et al. |
| 2016/0220315 A1 | 8/2016 | Falardeau et al. |
| 2016/0220320 A1 | 8/2016 | Crawford et al. |
| 2016/0220385 A1 | 8/2016 | Falardeau et al. |
| 2016/0228133 A1 | 8/2016 | Meridew et al. |
| 2016/0235490 A1 | 8/2016 | Srivastava et al. |
| 2016/0235492 A1 | 8/2016 | Morard et al. |
| 2016/0235493 A1 | 8/2016 | LeBoeuf, II et al. |
| 2016/0242860 A1 | 8/2016 | Diolaiti et al. |
| 2016/0242934 A1 | 8/2016 | van der Walt et al. |
| 2016/0256225 A1 | 9/2016 | Crawford et al. |
| 2016/0278865 A1 | 9/2016 | Capote et al. |
| 2016/0278875 A1 | 9/2016 | Crawford et al. |
| 2016/0278941 A1 | 9/2016 | Livorsi et al. |
| 2016/0296266 A1 | 10/2016 | Chandanson et al. |
| 2016/0310218 A1 | 10/2016 | Ruckel et al. |
| 2016/0310221 A1 | 10/2016 | Bar et al. |
| 2016/0331479 A1 | 11/2016 | Crawford |
| 2016/0331481 A1 | 11/2016 | Bonutti |
| 2016/0374769 A1 | 12/2016 | Schena et al. |
| 2017/0000505 A1 | 1/2017 | Moctezuma de la Barrera et al. |
| 2017/0007334 A1 | 1/2017 | Crawford et al. |
| 2017/0020630 A1 | 1/2017 | Johnson et al. |
| 2017/0027652 A1 | 2/2017 | Johnson et al. |
| 2017/0042620 A1 | 2/2017 | Bartelme et al. |
| 2017/0055940 A1 | 3/2017 | Shoham |
| 2017/0056086 A1 | 3/2017 | Kostrzewski et al. |
| 2017/0056116 A1 | 3/2017 | Kostrzewski |
| 2017/0065428 A1 | 3/2017 | Behzadi |
| 2017/0065432 A1 | 3/2017 | Singh |
| 2017/0071682 A1 | 3/2017 | Bar et al. |
| 2017/0071685 A1 | 3/2017 | Crawford et al. |
| 2017/0071691 A1 | 3/2017 | Crawford et al. |
| 2017/0071759 A1 | 3/2017 | Behzadi et al. |
| 2017/0079727 A1 | 3/2017 | Crawford et al. |
| 2017/0086896 A1 | 3/2017 | Crawford et al. |
| 2017/0086927 A1 | 3/2017 | Auld et al. |
| 2017/0086928 A1 | 3/2017 | Auld et al. |
| 2017/0086932 A1 | 3/2017 | Auld et al. |
| 2017/0100195 A1 | 4/2017 | Velusamy |
| 2017/0105846 A1 | 4/2017 | Behzadi |
| 2017/0108930 A1 | 4/2017 | Banerjee et al. |
| 2017/0119339 A1 | 5/2017 | Johnson et al. |
| 2017/0119472 A1 | 5/2017 | Herrmann et al. |
| 2017/0132789 A1 | 5/2017 | Deitz et al. |
| 2017/0143426 A1 | 5/2017 | Isaacs et al. |
| 2017/0143429 A1 | 5/2017 | Richmond et al. |
| 2017/0151025 A1 | 6/2017 | Mewes et al. |
| 2017/0156805 A1 | 6/2017 | Taylor et al. |
| 2017/0156816 A1 | 6/2017 | Ibrahim |
| 2017/0172669 A1 | 6/2017 | Berkowitz et al. |
| 2017/0172762 A1 | 6/2017 | Sherman et al. |
| 2017/0178349 A1 | 6/2017 | Ketcha et al. |
| 2017/0181774 A1 | 6/2017 | Cahill |
| 2017/0186180 A1 | 6/2017 | Piron et al. |
| 2017/0196506 A1 | 7/2017 | Behzadi |
| 2017/0196597 A1 | 7/2017 | Corbin et al. |
| 2017/0196599 A1 | 7/2017 | Kwon et al. |
| 2017/0196641 A1 | 7/2017 | Jagga et al. |
| 2017/0196701 A1 | 7/2017 | Behzadi et al. |
| 2017/0196705 A1 | 7/2017 | Behzadi |

(56)        References Cited

U.S. PATENT DOCUMENTS

| | | |
|---|---|---|
| 2017/0196706 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0202628 A1 | 7/2017 | Dell et al. |
| 2017/0202629 A1 | 7/2017 | Maillet et al. |
| 2017/0202683 A1 | 7/2017 | Behzadi |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224358 A1 | 8/2017 | Kostrzewski |
| 2017/0231702 A1 | 8/2017 | Crawford et al. |
| 2017/0239002 A1 | 8/2017 | Crawford et al. |
| 2017/0239003 A1 | 8/2017 | Crawford et al. |
| 2017/0239006 A1 | 8/2017 | Crawford et al. |
| 2017/0239007 A1 | 8/2017 | Crawford et al. |
| 2017/0239451 A1 | 8/2017 | Berkowitz |
| 2017/0239452 A1 | 8/2017 | Berkowitz et al. |
| 2017/0245951 A1 | 8/2017 | Crawford et al. |
| 2017/0252112 A1 | 9/2017 | Crawford et al. |
| 2017/0252114 A1 | 9/2017 | Crawford et al. |
| 2017/0258469 A1 | 9/2017 | Shelton, IV et al. |
| 2017/0258533 A1 | 9/2017 | Crawford et al. |
| 2017/0258535 A1 | 9/2017 | Crawford et al. |
| 2017/0261348 A1 | 9/2017 | LeBoeuf, II et al. |
| 2017/0265774 A1 | 9/2017 | Johnson et al. |
| 2017/0265872 A1 | 9/2017 | Otto et al. |
| 2017/0281145 A1 | 10/2017 | Crawford et al. |
| 2017/0290666 A1 | 10/2017 | Behzadi |
| 2017/0296274 A1 | 10/2017 | van der Walt et al. |
| 2017/0296276 A1 | 10/2017 | Bonutti |
| 2017/0312039 A1 | 11/2017 | Crawford et al. |
| 2017/0316561 A1 | 11/2017 | Helm et al. |
| 2017/0325892 A1 | 11/2017 | Aghazadeh |
| 2017/0333057 A1 | 11/2017 | Kostrzewski et al. |
| 2017/0333136 A1 | 11/2017 | Hladio et al. |
| 2017/0333137 A1 | 11/2017 | Roessler |
| 2017/0340448 A1 | 11/2017 | Behzadi |
| 2017/0340456 A1 | 11/2017 | Behzadi |
| 2017/0348037 A1 | 12/2017 | Sexson et al. |
| 2017/0354368 A1 | 12/2017 | Behzadi |
| 2017/0354468 A1 | 12/2017 | Johnson et al. |
| 2017/0360493 A1 | 12/2017 | Zucker et al. |
| 2017/0360575 A1 | 12/2017 | Behzadi et al. |
| 2017/0367847 A1 | 12/2017 | Piriou et al. |
| 2018/0000543 A1 | 1/2018 | Hibner |
| 2018/0008324 A1 | 1/2018 | Cryder et al. |
| 2018/0008353 A1 | 1/2018 | Kostrzewski et al. |
| 2018/0008358 A1 | 1/2018 | Kostrzewski et al. |
| 2018/0021058 A1 | 1/2018 | Meglan |
| 2018/0021096 A1 | 1/2018 | Kostrzewski et al. |
| 2018/0028270 A1 | 2/2018 | Itkowitz et al. |
| 2018/0042650 A1 | 2/2018 | Gao et al. |
| 2018/0042684 A1 | 2/2018 | Kostrzewski et al. |
| 2018/0049823 A1 | 2/2018 | Shelton, IV et al. |
| 2018/0049832 A1 | 2/2018 | Eckert et al. |
| 2018/0050454 A1 | 2/2018 | Linnell et al. |
| 2018/0078201 A1 | 3/2018 | Behzadi |
| 2018/0078266 A1 | 3/2018 | Fry et al. |
| 2018/0092648 A1 | 4/2018 | Sun et al. |
| 2018/0092757 A1 | 4/2018 | Behzadi et al. |
| 2018/0110573 A1 | 4/2018 | Kostrzewski |
| 2018/0111273 A1 | 4/2018 | Linnell et al. |
| 2018/0147018 A1 | 5/2018 | Crawford et al. |
| 2018/0168539 A1 | 6/2018 | Singh et al. |
| 2018/0168747 A1 | 6/2018 | Kopp et al. |
| 2018/0185100 A1 | 7/2018 | Weinstein et al. |
| 2018/0185107 A1 | 7/2018 | Nikou et al. |
| 2018/0193171 A1 | 7/2018 | van der Walt et al. |
| 2018/0199951 A1 | 7/2018 | Chappuis et al. |
| 2018/0199999 A1 | 7/2018 | Syverson et al. |
| 2018/0200002 A1 | 7/2018 | Kostrzewski et al. |
| 2018/0200016 A1 | 7/2018 | Chappuis et al. |
| 2018/0214223 A1 | 8/2018 | Turner |
| 2018/0221097 A1 | 8/2018 | Bonutti |
| 2018/0250077 A1 | 9/2018 | Xu et al. |
| 2018/0250086 A1 | 9/2018 | Grubbs |
| 2018/0250144 A1 | 9/2018 | Li et al. |
| 2018/0256259 A1 | 9/2018 | Crawford |
| 2018/0263714 A1 | 9/2018 | Kostrzewski et al. |
| 2018/0289432 A1 | 10/2018 | Kostrzewski et al. |
| 2018/0297211 A1* | 10/2018 | Schaible .............. B25J 13/025 |
| 2018/0325608 A1 | 11/2018 | Kang et al. |
| 2018/0353248 A1 | 12/2018 | Bowling et al. |
| 2019/0069882 A1 | 3/2019 | Moctezuma de la Barrera et al. |
| 2019/0076195 A1 | 3/2019 | Shalayev et al. |
| 2019/0090966 A1 | 3/2019 | Kang et al. |
| 2019/0159848 A1 | 5/2019 | Quaid et al. |
| 2019/0187804 A1 | 6/2019 | Linnell |
| 2019/0231447 A1 | 8/2019 | Ebbitt et al. |
| 2019/0269469 A1 | 9/2019 | Bush, Jr. et al. |
| 2020/0015917 A1 | 1/2020 | Cavalier et al. |
| 2020/0138498 A1 | 5/2020 | Chappuis et al. |
| 2020/0170724 A1 | 6/2020 | Flatt et al. |
| 2020/0205927 A1* | 7/2020 | Hunt ..................... A61B 34/37 |
| 2020/0223074 A1 | 7/2020 | Bohle, II |
| 2020/0281676 A1 | 9/2020 | Rohs et al. |
| 2020/0375675 A1 | 12/2020 | Patriciu et al. |
| 2021/0015564 A1 | 1/2021 | Vogele |
| 2021/0229278 A1 | 7/2021 | Gillespie et al. |
| 2021/0275260 A1 | 9/2021 | Kang et al. |
| 2021/0298795 A1 | 9/2021 | Bowling et al. |
| 2021/0307849 A1 | 10/2021 | Kang |
| 2022/0061934 A1 | 3/2022 | Sen et al. |
| 2022/0079688 A1 | 3/2022 | Kostrzewski et al. |
| 2022/0240996 A1 | 8/2022 | Chappuis et al. |
| 2022/0273378 A1* | 9/2022 | Soto ..................... A61B 34/37 |
| 2023/0104580 A1* | 4/2023 | Roh ..................... A61F 7/0097 |
| | | 128/848 |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 0203370 A1 | 12/1986 |
| KR | 20170129995 A | 11/2017 |
| WO | 2003090974 A1 | 11/2003 |
| WO | 2005039391 A2 | 5/2005 |
| WO | 2009092164 A1 | 7/2009 |
| WO | 2011062910 A1 | 5/2011 |
| WO | 2011063715 A1 | 6/2011 |
| WO | 2013075500 A1 | 5/2013 |
| WO | 2013192598 A1 | 12/2013 |
| WO | 2014138916 A1 | 9/2014 |
| WO | 2014139023 A1 | 9/2014 |
| WO | 2014139024 A1 | 9/2014 |
| WO | 2015061638 A1 | 4/2015 |
| WO | 2015087335 A1 | 6/2015 |
| WO | 2015115807 A1 | 8/2015 |
| WO | 2015115809 A1 | 8/2015 |
| WO | 2015166487 A1 | 11/2015 |
| WO | 2015193479 A1 | 12/2015 |
| WO | 2016008880 A1 | 1/2016 |
| WO | 2016042152 A1 | 3/2016 |
| WO | 2016088130 A1 | 6/2016 |
| WO | 2016115423 A1 | 7/2016 |
| WO | 2016118744 A1 | 7/2016 |
| WO | 2017001851 A1 | 1/2017 |
| WO | 2017023825 A1 | 2/2017 |
| WO | 2017027331 A1 | 2/2017 |
| WO | 2017035592 A1 | 3/2017 |
| WO | 2017036340 A1 | 3/2017 |
| WO | 2017037113 A1 | 3/2017 |
| WO | 2017037127 A1 | 3/2017 |
| WO | 2017043926 A1 | 3/2017 |
| WO | 2017048736 A1 | 3/2017 |
| WO | 2017064719 A1 | 4/2017 |
| WO | 2017115227 A1 | 7/2017 |
| WO | 2017121874 A2 | 7/2017 |
| WO | 2017122202 A1 | 7/2017 |
| WO | 2017123506 A1 | 7/2017 |
| WO | 2017136550 A1 | 8/2017 |
| WO | 2017123506 A9 | 9/2017 |

(56) References Cited

FOREIGN PATENT DOCUMENTS

| WO | 2017151607 A1 | 9/2017 |
| WO | 2017162981 A1 | 9/2017 |
| WO | 2017177046 A1 | 10/2017 |
| WO | 2017211950 A1 | 12/2017 |
| WO | 2017218423 A1 | 12/2017 |
| WO | 2017219207 A1 | 12/2017 |
| WO | 2017219208 A1 | 12/2017 |
| WO | 2018031752 A1 | 2/2018 |
| WO | 2018067784 A1 | 4/2018 |
| WO | 2018072003 A1 | 4/2018 |
| WO | 2019100148 A1 | 5/2019 |
| WO | 2020181290 A1 | 9/2020 |
| WO | 2021067438 A1 | 4/2021 |
| WO | 2022076773 A1 | 4/2022 |

OTHER PUBLICATIONS

Abstract of Campbell, EM, "Multiterawatt Nd: Glass Lasers Based on Chirped-Pulsed Amplification", Femtosecond and Nanosecond High-Intensity Lasers and Applications, Society of Photo-Optical Instrumentation Engineers, Los Angeles, California/Bellingham, WA, SPIE; Jan. 17-18, 1990, 4 pages.

Adogwa, O. et al., "Comparative Effectiveness of Minimally Invasive Versus Open Transforaminal Lumbar Interbody Fusion: 2-Year Assessment of Narcotic Use, Return to Work, Disability, and Quality of Life", J. Spinal Disord. Tech., vol. 24, 2011, pp. 479-484.

Amini-Nik, S. et al., "Ultrafast Mid-IR Laser Scalpel: Protein Signals of the Fundamental Limits to Minimally Invasive Surgery", PLoS ONE, vol. 5, No. 9, 2010, 6 pages.

Antipov, Oleg et al., "Highly Efficient 2???m CW and Q-Switched Tm3+:Lu2O3 Ceramics Lasers In-Band Pumped by a Raman-Shifted Erbium Fiber Laser at 1670??nm", Opt. Lett. 41, 2016, pp. 2298-2301.

Devito, DP et al., Clinical Acceptance and Accuracy Assessment of Spinal Implants Guided with the SpineAssist Surgical Robot—Retrospective Study, Spine, vol. 35, No. 24, 2010, pp. 2109-2115.

English language abstract and machine-assisted English translation (of equivalent CN 103126767) for WO 2013/075500 extracted from espacenet.com database on Nov. 28, 2018, 12 pages.

English language abstract and machine-assisted English translation for CN 101579269 extracted from espacenet.com database on Oct. 1, 2018, 11 pages.

English language abstract and machine-assisted English translation for CN 101700184 extracted from espacenet.com database on Oct. 1, 2018, 15 pages.

English language abstract and machine-assisted English translation for CN 101853333 extracted from espacenet.com database on Oct. 1, 2018, 13 pages.

English language abstract and machine-assisted English translation for CN 201422918 extracted from espacenet.com database on Oct. 1, 2018, 11 pages.

English language abstract and machine-assisted English translation for CN 201542641 extracted from espacenet.com database on Oct. 1, 2018, 15 pages.

English language abstract and machine-assisted English translation for EP 0 203 370 A1 extracted from espacenet.com database on Apr. 5, 2021, 10 pages.

English language abstract and machine-assisted English translation for KR 20170129995 A extracted from espacenet.com database on Jun. 30, 2021, 12 pages.

English language abstract and machine-assisted English translation for WO 2015/115807 A1 extracted from espacenet.com database on Apr. 5, 2021, 9 pages.

English language abstract and machine-assisted English translation for WO 2015/115807 extracted from espacenet.com database on Nov. 28, 2018, 16 pages.

English language abstract and machine-assisted English translation for WO 2015/115809 extracted from espacenet.com database on Oct. 1, 2018, 14 pages.

English language abstract and machine-assisted English translation for WO 2017/043926 A1 extracted from espacenet.com database on Jun. 30, 2021, 19 pages.

English language abstract and machine-assisted English translation for WO 2017/162981 extracted from espacenet.com database on Oct. 1, 2018, 13 pages.

English language abstract and machine-assisted English translation for WO 2017/219207 A1 extracted from espacenet.com database on Apr. 5, 2021, 11 pages.

English language abstract and machine-assisted English translation for WO 2017/219207 extracted from espacenet.com database on Nov. 28, 2018, 14 pages.

English language abstract and machine-assisted English translation for WO 2017/219208 A1 extracted from espacenet.com database on Apr. 5, 2021, 6 pages.

International Search Report for Application No. PCT/US2018/031999 dated Nov. 7, 2018, 5 pages.

International Search Report for Application No. PCT/US2019/060502 dated Apr. 6, 2020, 4 pages.

International Search Report for Application No. PCT/US2021/024438 dated Sep. 24, 2021, 5 pages.

Invitation to Pay Additional Fees and Partial Search Report for Application No. PCT/US2018/031999 dated Sep. 12, 2018, 3 pages.

Kotani, Y. et al., "Mid-Term Clinical Results of Minimally Invasive Decompression and Posterolateral Fusion With Percutaneous Pedicle Screws Versus Conventional Approach For Degenerative Spondylolisthesis With Spinal Stenosis", Eur. Spine J., vol. 21, 2012, pp. 1171-1177.

Lee, P. et al., "Perioperative and Postoperative Complications of Single-Level Minimally Invasive Transforaminal Lumbar Interbody Fusion in Elderly Adults", J. Clin. Neurosci., vol. 19, 2012;, pp. 111-114.

Lorensen, William E. et al., "Marching Cubes: A High Resolution 3D Surface Construction Algorithm", ACM Siggraph Computer Graphics, vol. 21, No. 4, ACM, 1987, 7 pages.

Mahvash, M. et al., "Modeling the Forces of Cutting With Scissors", IEEE Trans. Biomed. Eng., vol. 55, No. 3, 2008, pp. 848-856.

McGirt MJ et al., "Comparative Analysis of Perioperative Surgical Site Infection After Minimally Invasive Versus Open Posterior/Transforaminal Lumbar Interbody Fusion: Analysis of Hospital Billing and Discharge Data from 5,170 patients", J. Neurosurg. Spine, vol. 14, 2011, pp. 771-778.

Roble De-La-Torre, Gabriel, "The Importance of the Sense of Touch in Virtual and Real Environments", International Society for Haptics, IEEE 2006, 7 pages.

Romero, Francisco et al., "Experimental and Analytical Validation of a Modular Acetabular Prosthesis in Total Hip Arthroplasty", Journal of Orthopaedic Surgery and Research, May 16, 2007, pp. 1-9.

Sakai, Y et al., "Segmental Pedicle Screwing For Idiopathic Scoliosis Using Computer-Assisted Surgery", J. Spinal Disord. Tech., vol. 21, 2008, pp. 181-186.

Vogel, A. et al., "Mechanisms of Pulsed Laser Ablation of Biological Tissues", Chem. Rev., vol. 103, No. 2, 2003, pp. 577-644.

* cited by examiner

ISOLATED MANUAL MODE

NON-ISOLATED MANUAL MODE

AUTOMATED MODE

SURGICAL ROBOTIC SYSTEM WITH COMPLIANCE MECHANISM

CROSS-REFERENCE TO RELATED APPLICATIONS

The subject application claims priority to and all the benefits of U.S. Provisional Patent App. No. 63/348,633, filed Jun. 3, 2022, the entire contents of which are hereby incorporated by reference.

BACKGROUND

Robotic systems are commonly utilized to perform surgical procedures. The robotic system typically has a robotic arm that supports a surgical tool to manipulate or treat the surgical site. One type of robotic system is an admittance system which controls position of the surgical tool based on an input force. The input force can be detected using a force/torque sensor that is disposed at the distal flange of the robotic arm to detect forces/torques applied to the surgical tool by a user controlling the robot. This force/torque sensor is typically quite stiff to enable the sensor to stably support the surgical tool relative during movement of the robotic arm and to enable the surgical tool accurately reach the commanded position.

Admittance-control systems may be susceptible to error where the surgical tool is commanded to a position where the environment is stiff. For instance, the robot may move the surgical tool to a commanded position, and in so doing, the surgical tool may abruptly contact the surgical site or improperly engage the surgical site due to circumstances unforeseen by the robot controller. This issue is particularly relevant where the surgical tool is used to cut or drill into a bone or install an implant into a bone. In turn, the physical reactive force occurring due to such abrupt contact or improper engagement may be detected by the force/torque sensor at the distal flange of the robotic arm. However, the force/torque sensor is overly stiff and does not provide compliance to absorb displacement of the surgical tool resulting from the hard contact. As a result, the surgical tool may be subsequently commanded based on a force/torque sensor reading that is derived from an error condition thereby resulting in non-optimal or unstable performance.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a surgical system is provided comprising: a robotic manipulator; an end effector supported by the robotic manipulator, the end effector comprising: a surgical tool configured to interact with an anatomy; and a compliance mechanism configured to enable the surgical tool to move relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; and an input device comprising a first force/torque portion; and an input device comprising a first force/torque sensor configured to sense a force/torque applied to the input device by a user, wherein the first force/torque sensor is mechanically isolated from the external forces/torques applied to the surgical tool.

According to a second aspect, a method of operating a surgical system is provided, the surgical system comprising a control system, a robotic manipulator, an end effector supported by the robotic manipulator, the end effector comprising a surgical tool configured to interact with an anatomy and a compliance mechanism configured to enable the surgical tool to move relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion, and the end effector including an input device comprising a first force/torque sensor, the method comprising: controlling, with the control system, the robotic manipulator to move the surgical tool to interact with the anatomy such that external forces/torques are applied to the surgical tool by the anatomy; enabling, with the compliance mechanism, the surgical tool to move relative to the robotic manipulator in response to the external forces/torques applied to the surgical tool by the anatomy; sensing, with the first force/torque sensor, a force/torque applied to the input device by a user, wherein the first force/torque sensor is mechanically isolated from the external forces/torques applied to the surgical tool; and controlling, with the control system, the robotic manipulator to move the surgical tool based on the force/torque applied to the input device by the user.

According to a third aspect, an end effector for a surgical system is provided, the end effector being configured to be supported by a robotic manipulator, the end effector comprising: a surgical tool; a compliance mechanism configured to enable the surgical tool to move relative to the robotic manipulator in response to external forces/torques applied to the surgical tool, the compliance mechanism comprising a stationary portion coupled to the robotic manipulator, a moveable portion coupled to the surgical tool, and a flexible portion disposed between the stationary portion and the moveable portion; and an input device comprising a first force/torque sensor configured to sense a force/torque applied to the input device by a user, wherein the first force/torque sensor is mechanically isolated from the external forces/torques applied to the surgical tool.

According to a fourth aspect, a surgical system is provided comprising: a robotic manipulator; a surgical tool supported by the robotic manipulator; a compliance mechanism configured to enable the surgical tool to move relative to the robotic manipulator in response to external forces/torques applied to the surgical tool, the compliance mechanism comprising a stationary portion coupled to the robotic manipulator, a moveable portion coupled to the surgical tool, and a flexible portion disposed between the stationary portion and the moveable portion; and an input device comprising a first force/torque sensor configured to sense a force/torque applied to the input device by a user, wherein the first force/torque sensor is mechanically isolated from the external forces/torques applied to the surgical tool.

According to a fifth aspect, a method of operating the surgical system of the fourth aspect is provided.

According to a sixth aspect, a surgical system is provided comprising: a robotic manipulator; a surgical tool supported by the robotic manipulator and being configured to interact with an anatomy, the surgical tool comprising a tool axis; a compliance mechanism configured to enable the surgical tool to experience a linear displacement relative to the robotic manipulator in response to external forces/torques applied to the surgical tool by the anatomy, the linear displacement being parallel, or coincident, to the tool axis, the compliance mechanism comprising a stationary portion coupled to the robotic manipulator, a moveable portion coupled to the surgical tool, and a flexible portion disposed between the stationary portion and the moveable portion; an input device comprising a sensor configured to sense a user input; and a control system configured to command linear movement of the surgical tool with the robotic manipulator based on the user input, the commanded linear movement being parallel to the tool axis.

According to a seventh aspect, a method of operating the surgical system of the sixth aspect is provided.

According to an eighth aspect, a surgical system is provided comprising: a robotic manipulator; a surgical tool supported by the robotic manipulator and being configured to interact with an anatomy; a force/torque sensor coupled between the robotic manipulator and the surgical tool, the force/torque sensor configured to sense external forces/torques applied to the surgical tool by a user; an input device coupled to the surgical tool and comprising a input device sensor configured to sense a force/torque applied to the input device by the user, wherein the input device sensor is mechanically isolated from the external forces/torques applied to the surgical tool; and a control system configured to control movement of the surgical tool with the robotic manipulator in: a non-isolated manual mode in which the robotic manipulator is commanded based on external forces/torques applied to the surgical tool by the user, the external forces/torques being sensed by the force/torque sensor; and an isolated manual mode in which the robotic manipulator is commanded based on the force/torque applied to the input device by the user, the applied force/torque being sensed by the input device sensor.

According to a ninth aspect, a method of operating the surgical system of the eighth aspect is provided.

According to a tenth aspect, a surgical system is provided comprising: a robotic manipulator; a surgical tool supported by the robotic manipulator and being configured to interact with an anatomy, the surgical tool comprises a tool axis; and a force/torque sensor coupled between the robotic manipulator and the surgical tool, the force/torque sensor configured to sense external forces/torques applied to the surgical tool by a user; an input device sensor coupled to the surgical tool and configured to sense a user input, wherein the input device sensor is mechanically isolated from the external forces/torques applied to the surgical tool; a navigation system is configured to track the anatomy and register a planned trajectory to the anatomy; and a control system coupled to the navigation system and being configured to control movement of the surgical tool with the robotic manipulator in: a non-isolated manual mode to enable the user to move the surgical tool towards the anatomy along the planned trajectory while the surgical tool is constrained by the planned trajectory, wherein in the non-isolated manual mode, the robotic manipulator is commanded based on external forces/torques applied to the surgical tool by the user, the external forces/torques being sensed by the force/torque sensor; and an isolated manual mode to enable the user to move the surgical tool towards the anatomy along the planned trajectory while the surgical tool is constrained by the planned trajectory, wherein in the isolated manual mode the robotic manipulator is commanded based on the user input sensed by the input device sensor.

According to an eleventh aspect, a method of operating the surgical system of the tenth aspect is provided.

According to a twelfth aspect, a surgical system is provided comprising: a robotic manipulator; a surgical tool supported by the robotic manipulator and being configured to interact with an anatomy; a force/torque sensor coupled between the robotic manipulator and the surgical tool, the force/torque sensor configured to sense external forces/torques applied to the surgical tool by a user; an input device sensor coupled to the surgical tool and configured to sense a user input, wherein the input device sensor is mechanically isolated from the external forces/torques applied to the surgical tool; a compliance mechanism configured to enable the surgical tool to experience a displacement relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; a displacement sensor configured to measure the displacement of the surgical tool relative to the robotic manipulator; and a control system configured to: control movement of the surgical tool with the robotic manipulator in a non-isolated manual mode to enable the user to move the surgical tool towards the anatomy, wherein in the non-isolated manual mode, the robotic manipulator is commanded based on external forces/torques applied to the surgical tool by the user, the external forces/torques being sensed by the force/torque sensor, and in the non-isolated manual mode, the surgical tool experiences external forces/torques applied by the anatomy causing the surgical tool to experience the displacement relative to the stationary portion; evaluate the displacement measured by the displacement sensor relative to a threshold, the threshold being one or both of: a threshold displacement and a threshold duration of displacement; and in response to determining that the measured displacement exceeds the threshold, deactivate the non-isolated manual mode and activate an isolated manual mode in which the surgical tool is controlled with the robotic manipulator to enable the user to move the surgical tool towards the anatomy and the robotic manipulator is commanded based on the user input sensed by the input device sensor.

According to a thirteenth aspect, a method of operating the surgical system of the twelfth aspect is provided.

According to a fourteenth aspect, a surgical system is provided comprising: a robotic manipulator; a surgical tool supported by the robotic manipulator; and a compliance mechanism configured to enable the surgical tool to move relative to the robotic manipulator in response to external forces/torques applied to the surgical tool, the compliance mechanism comprising a stationary portion coupled to the robotic manipulator, a moveable portion coupled to the surgical tool, and a flexible portion disposed between the stationary portion and the moveable portion.

According to a fifteenth aspect, a method of operating the surgical system of the fourteenth aspect is provided.

According to a sixteenth aspect, a surgical system is provided comprising: a robotic manipulator; a surgical tool supported by the robotic manipulator and being configured to interact with an anatomy; a force/torque sensor coupled between the robotic manipulator and the surgical tool, the force/torque sensor configured to sense external forces/torques applied to the surgical tool by a user; an input device coupled to the surgical tool and comprising an input device sensor configured to sense a force/torque applied to the input device by the user, wherein the input device sensor is mechanically isolated from the external forces/torques applied to the surgical tool; a control system configured to: define virtual constraints on movement of the surgical tool; simulate dynamics of the surgical tool in a virtual simulation based on the virtual constraints and the external forces/torques being sensed by the force/torque sensor, wherein the force/torque sensed by the input device sensor is excluded from the virtual simulation; and control movement of the surgical tool with the robotic manipulator based on the virtual simulation.

According to a seventeenth aspect, a method of operating the surgical system of the sixteenth aspect is provided.

According to an eighteenth aspect, a surgical system is provided comprising: a robotic manipulator; a surgical tool supported by the robotic manipulator and being configured to interact with an anatomy; a first sensor coupled between the robotic manipulator and the surgical tool, the first sensor configured to sense external forces/torques applied to the surgical tool by a user, wherein the first sensor is a six degree of freedom (DOF) load cell; and an input device coupled to the surgical tool and comprising an input device sensor configured to sense a force/torque applied to the input device by the user, wherein the input device sensor is a single DOF load cell and is mechanically isolated from the external forces/torques applied to the surgical tool.

According to a nineteenth aspect, a method of operating the surgical system of the eighteenth aspect is provided.

According to a twentieth aspect, a surgical system is provided comprising: a robotic manipulator; a surgical tool supported by the robotic manipulator and being configured to interact with an anatomy, the surgical tool is configured to hold a screw and to rotate the screw about a rotational axis, the screw having a known thread geometry; a compliance mechanism configured to enable the surgical tool to experience a displacement relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; a sensor configured to measure the displacement of the surgical tool relative to the robotic manipulator; and a control system comprising a memory for storing the known thread geometry and being configured to: control the robotic manipulator to command a rotational rate of the surgical tool to rotate the screw about the rotational axis and to command a displacement of the surgical tool to advance the screw towards the anatomy, wherein the rotational rate and the displacement of the surgical tool are each proportional to the known thread geometry stored in the memory; and pursuant to the robotic manipulator commanding the rotational rate and displacement of the surgical tool to advance the screw towards the anatomy, detect, from the sensor, that the surgical tool has experienced the displacement relative to the robotic manipulator and generate an alert indicative of the screw improperly engaging the anatomy.

According to a twenty-first aspect, a method of operating the surgical system of the twentieth aspect is provided.

According to a twenty-second aspect, a surgical system is provided comprising: a robotic manipulator; a surgical tool supported by the robotic manipulator and being configured to interact with an anatomy, the surgical tool is configured to hold a screw and to rotate the screw about a rotational axis, the screw having a known thread geometry; a navigation system configured to track the anatomy and generate tracking data; and a control system comprising a memory for storing the known thread geometry and being configured to: control the robotic manipulator to command a rotational rate of the surgical tool to rotate the screw about the rotational axis and to command a displacement of the surgical tool to advance the screw towards the anatomy, wherein the rotational rate and the displacement of the surgical tool are each proportional to the known thread geometry stored in the memory; and compare the tracking data from the navigation system with the commanded displacement to detect an error related to engagement between the screw and the anatomy.

According to a twenty-third aspect, a method of operating the surgical system of the twenty-second aspect is provided.

According to a twenty-fourth aspect, a surgical system is provided comprising: a robotic manipulator; a surgical tool supported by the robotic manipulator and being configured to interact with an anatomy; a force/torque sensor coupled between the robotic manipulator and the surgical tool, the force/torque sensor configured to sense external forces/torques applied to the surgical tool by a user; a compliance mechanism configured to enable the surgical tool to experience a displacement relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; a sensor configured to measure the displacement of the surgical tool relative to the robotic manipulator; and a control system is configured to: detect, from the sensor, the displacement of the surgical tool relative to the robotic manipulator; and control movement of the surgical tool with the robotic manipulator based on the detected displacement.

According to a twenty-fifth aspect, a method of operating the surgical system of the twenty-fourth aspect is provided.

According to a twenty-sixth aspect, a surgical system is provided comprising: a robotic manipulator; a surgical tool supported by the robotic manipulator; a compliance mechanism configured to enable the surgical tool to move relative to the robotic manipulator in response to external forces/torques applied to the surgical tool, the compliance mechanism comprising a stationary portion coupled to the robotic manipulator, a moveable portion coupled to the surgical tool, and a flexible portion disposed between the stationary portion and the moveable portion; and a force/torque sensor coupled to the flexible portion and being configured to detect external forces/torques applied to the surgical tool.

According to a twenty-seventh aspect, a method of operating the surgical system of the twenty-sixth aspect is provided.

According to a twenty-eighth aspect, a surgical system is provided comprising: a robotic manipulator; a surgical tool supported by the robotic manipulator and being configured to interact with an anatomy that has an anatomical feature that is either natural or artificially created; a force/torque sensor coupled between the robotic manipulator and the surgical tool, the force/torque sensor configured to sense external forces/torques applied to the surgical tool; and a control system is configured to: control movement of the surgical tool with the robotic manipulator to interact with the anatomy and the anatomical feature; detect, from the force/torque sensor, the external forces/torques applied to the surgical tool during interaction with anatomy and the anatomical feature; and based on the detected external forces/torques, determine coordinates of the anatomical feature relative to the anatomy According to a twenty-ninth aspect, a method of operating the surgical system of the twenty-eighth aspect is provided.

According to a thirtieth aspect, a surgical system is provided comprising: a robotic manipulator; a surgical tool supported by the robotic manipulator and being configured to interact with an anatomy that has an anatomical feature that is either natural or artificially created; a compliance mechanism configured to enable the surgical tool to experience a displacement relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; a sensor configured to measure the displacement of the surgical tool relative to the robotic manipulator; and a control system is configured to: control movement of the surgical tool with the robotic manipulator to interact with the anatomy and the anatomical feature; detect, from the sensor, the displacements of the surgical tool relative to the robotic manipulator during interaction with anatomy and the anatomical feature; and based on the detected displacements, determine coordinates of the anatomical feature relative to the anatomy.

According to a thirty-first aspect, a method of operating the surgical system of the thirtieth aspect is provided.

Any of the above aspects can be utilized individually, or in combination.

Any of the above aspects can be utilized with any of the following implementations:

In one implementation, the control system is configured to control movement of the surgical tool with the robotic manipulator in an isolated manual mode in which the robotic manipulator is commanded based on the force/torque applied to the input device by the user, the applied force/torque being sensed by the first force/torque sensor. In one implementation, the surgical tool is configured to hold a screw and to rotate the screw about a rotational axis, the screw having a known thread geometry. In one implementation, the screw is a pedicle screw. In one implementation, the screw is self-tapping. In one implementation, the control system comprises a memory for storing the known thread geometry. In one implementation, based on the force/torque applied to the input device by the user, the control system is configured to control, in the isolated manual mode, a rotational rate of the surgical tool to rotate the screw about the rotational axis and/or to control a linear displacement of the surgical tool to advance the screw. In one implementation, the rotational rate and the linear displacement of the surgical tool are each proportional to the known thread geometry stored in the memory. In one implementation, input device sensor is a (first) force/torque sensor or a 1DOF load cell. In one implementation, the input device sensor is a displacement sensor. In one implementation, the input device is a control lever extending away from the body of the tool. In one implementation, the control system is configured to control 1DOF movement of the surgical tool with the robotic manipulator in the isolated manual mode. In one implementation, a (second) force/torque sensor is coupled between the robotic manipulator and the end effector, and optionally, at a distal flange of the manipulator. In one implementation, the second force/torque sensor is configured to sense external forces/torques applied to the end effector or the surgical tool. In one implementation, the external forces/torques are applied by the user or by the anatomy. In one implementation, the control system is configured to control movement of the surgical tool with the robotic manipulator in a non-isolated manual mode in which the robotic manipulator is commanded based on external forces/torques applied to the end effector or the surgical tool by the user, the external forces/torques being sensed by the second force/torque sensor. In one implementation, the control system is configured to define virtual constraints on movement of the surgical tool. In one implementation, the control system simulates dynamics of the surgical tool in a virtual simulation based on the virtual constraints and the external forces/torques being sensed by the second force/torque sensor. In one implementation, the control system controls movement of the surgical tool with the robotic manipulator based on the virtual simulation. In one implementation, the force/torque sensed by the first force/torque sensor is excluded from the virtual simulation. In one implementation, the second force/torque sensor is a 6DOF load cell. In one implementation, the control system is configured to control movement of the surgical tool in at least 1DOF with the robotic manipulator in the non-isolated manual mode. In one implementation, the control system is configured to detect a condition, and in response to detection of the condition: activate the isolated manual mode and deactivate the non-isolated manual mode; deactivate the isolated manual mode and activate the non-isolated manual mode; or combine control using both the isolated manual mode and the non-isolated manual mode. In one implementation, a navigation system is configured to track a distance between the surgical tool and the anatomy. In one implementation, the control system deactivates the isolated manual mode and activate the non-isolated manual mode and controls movement of the surgical tool with the robotic manipulator in the non-isolated manual mode to enable the user to move the surgical tool towards the anatomy. In one implementation, the control system detects the condition being the distance between the surgical tool and the anatomy satisfying a threshold distance during control in the non-isolated manual mode. In one implementation, the control system in response to detection of the condition, deactivates the non-isolated manual mode and activate the isolated manual mode. In one implementation, the control system controls movement of the surgical tool with the robotic manipulator in the isolated manual mode to enable the user to move the surgical tool towards the anatomy. In one implementation, the surgical tool comprises a tool axis. In one implementation, a navigation system is configured to track the anatomy and register a planned trajectory to the anatomy. In one implementation, the planned trajectory is a line for a drill, saw, bur, screw, or screwdriver. In one implementation, the planned trajectory is a cutting plane for a saw. In one implementation, the control system controls movement of the surgical tool with the robotic manipulator in the isolated manual mode to enable the user to move the surgical tool towards the anatomy along the planned trajectory while the surgical tool is constrained by the planned trajectory. In one implementation, the control system controls movement of the surgical tool with the robotic manipulator in the non-isolated manual mode to enable the user to (1) move the surgical tool from a first position off the planned trajectory to a second position on the planned trajectory; and/or (2) move the surgical tool towards the anatomy along the planned trajectory while the surgical tool is constrained by the planned trajectory. In one implementation, the control system controls movement of the surgical tool with the robotic manipulator in the non-isolated manual mode to enable the user to move the surgical tool to engage the anatomy along the planned trajectory while the surgical tool is constrained by the planned trajectory. In one implementation, in the non-isolated manual mode, the surgical tool experiences external forces/torques applied by the anatomy. In one implementation, in response to the external forces/torques applied to the surgical tool by the anatomy, the moveable portion is configured to experience a displacement relative to the stationary portion. In one implementation, a sensor is configured to measure the displacement of the moveable portion relative to the stationary portion. In one implementation, the control system evaluates the displacement measured by the sensor. In one implementation, the control system evaluates the displacement measured by the sensor relative to a threshold. In one implementation, the threshold is one or both of: a threshold displacement and a threshold duration of displacement. In one implementation, the control system determines that the displacement measured by the sensor exceeds the threshold, and in response, the control system is configured to perform one or more of the following: constrain movement of the robotic manipulator in the non-isolated manual mode to prevent the user from moving the surgical tool towards the anatomy along the planned trajectory; deactivate the non-isolated manual mode; activate the isolated manual mode; control the robotic manipulator to move the surgical tool off the planned trajectory; and disable operation of the robotic manipulator. In one implementation, the control system determines that the displacement measured by the sensor does not exceed the threshold, and in response, the control system is configured to permit or resume movement of the robotic manipulator in the non-isolated manual mode to enable the user to move the surgical tool towards the anatomy along the planned trajectory. In one implementation, the control system controls movement of the surgical tool with the robotic manipulator in the isolated manual mode to enable the user to move the surgical tool to engage the anatomy along the planned trajectory while the surgical tool is constrained by the planned trajectory. In one implementation, in the isolated manual mode, the surgical tool experiences external forces/torques applied by the anatomy. In one implementation, in response to the external forces/torques applied to the surgical tool by the anatomy, the moveable portion is configured to experience a displacement relative to the stationary portion. In one implementation, a sensor is configured to measure the displacement of the moveable portion relative to the stationary portion. In one implementation, the control system controls the robotic manipulator based on the displacement measured by the sensor. In one implementation, the control system controls movement of the surgical tool with the robotic manipulator in an automated mode, and optionally, to automatically maintain the tool axis on the planned trajectory, and/or to automatically move the surgical tool from a first position off the planned trajectory to a second position on the planned trajectory. In one implementation, the control system controls movement of the surgical tool with the robotic manipulator in the automated mode to automatically maintain the tool axis on the planned trajectory while simultaneously: controlling movement of the surgical tool with the robotic manipulator in the isolated manual mode to enable the user to move the surgical tool towards the anatomy along the planned trajectory while the surgical tool is constrained by the planned trajectory; and/or controlling movement of the surgical tool with the robotic manipulator in the non-isolated manual mode to enable the user to move the surgical tool towards the anatomy along the planned trajectory while the surgical tool is constrained by the planned trajectory. In one implementation, in response to external forces/torques applied to the surgical tool by the anatomy, the compliance mechanism enables the surgical tool to move relative to the robotic manipulator in an axial direction that is parallel to, or coincident with, the tool axis. In one implementation, the compliance mechanism is configured to be self-centering or self-neutralizing such that the moveable portion is in a neutral position in an absence of external forces/torques applied to the surgical tool, is in a loaded position as external forces/torques are applied to the surgical tool and returns to the neutral position in response to external forces/torques no longer being applied to the surgical tool. In one implementation, the stationary portion comprises an upper platform and a lower platform and a rail extending between the upper platform and the lower platform. In one implementation, the rail is oriented in a direction that is parallel to, or coincident with, the tool axis. In one implementation, the moveable portion comprises a body with an upper surface and a lower surface and the body defines a channel that extends from the upper surface to the lower surface. In one implementation, the rail is disposed through the channel. In one implementation, the moveable portion is configured to slide along the rail between the upper platform and lower platform of the stationary portion and slide in a direction parallel to, or coincident with, the tool axis. In one implementation, the flexible portion comprises a biasing device. In one implementation, the biasing device is disposed between the upper platform and the upper surface or disposed between the lower platform and the lower surface. In one implementation, the compliance mechanism has a locking mechanism to selectively fix the position of the moveable portion. In one implementation, the compliance mechanism has a stopper that can be positioned to selectively adjust allowable displacement. In one implementation, the compliance mechanism is detachable from the end effector. In one implementation, the compliance mechanism is integrated into the end effector. In one implementation, the robotic manipulator comprises a robotic arm including a plurality of links and joints, and wherein the end effector is coupled to the robot arm. In one implementation, the end effector detachably mounts to a distal flange of the manipulator. In one implementation, the robotic manipulator is hand-held such that a user supports the robotic manipulator against a force of gravity, the robotic manipulator comprising a grasping portion configured to be grasped by the user, and an actuatable portion that is configured to move relative to the grasping portion, wherein the end effector is coupled to the actuatable portion. In one implementation, the tool is a screwdriver, and optionally, a multi-speed screwdriver. In one implementation, the tool can hold a pedicle screw and release the pedicle screw. In one implementation, the tool is a saw.

These and other features will be more clearly understood from the following detailed description taken in conjunction with the accompanying drawings and claims.

DETAILED DESCRIPTION

I. Example System Overview

Referring to the Figures, wherein like numerals indicate like or corresponding parts throughout the several views, a surgical system 10 (hereinafter "system") and method for operating the system 10 are described herein and shown throughout the accompanying figures.

Figure 1:
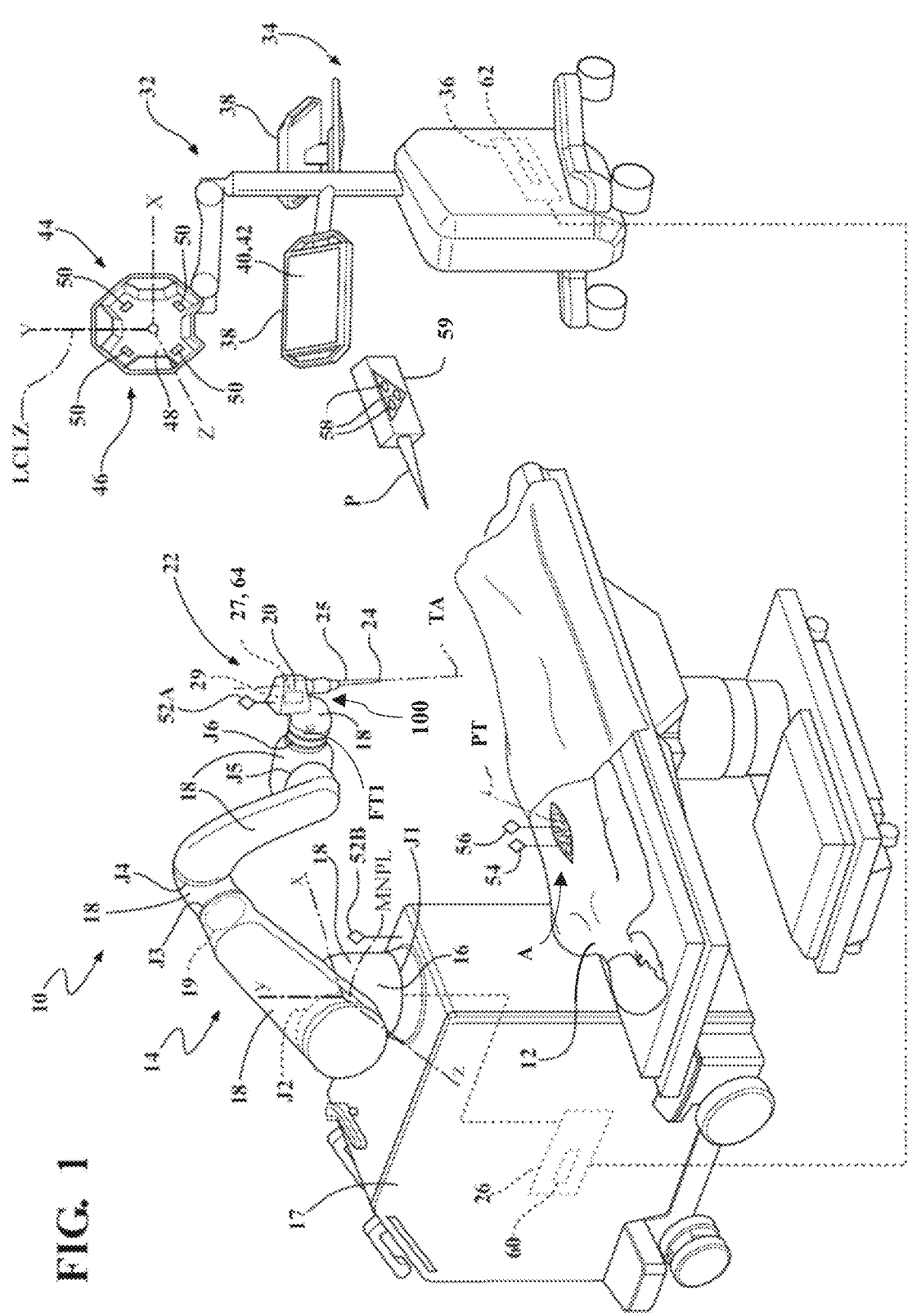
FIG. 1 is a perspective view of a surgical system comprising a robotic manipulator and navigation system, according to one implementation.

As shown in FIG. 1, the system 10 is a robotic surgical system for treating an anatomy (A) (surgical site) of a patient 12, such as bone or soft tissue. In FIG. 1, the patient 12 is undergoing a surgical procedure. The anatomy (A) in FIG. 1 includes a spine of the patient 12. The surgical procedure may involve tissue removal or treatment. The system 10, according to one aspect, is configured to prepare the anatomy (A) for insertion of pedicle screws and implant the pedicle screws into one or more vertebral bodies. Robotic systems, tools, and techniques for preparing for and installing pedicle screws can be like those described in U.S. patent application Ser. No. 16/184,376, filed Nov. 8, 2018, entitled "Robotic Spine Surgery System and Methods," the entire contents of which are hereby incorporated by reference.

The techniques and advantages described herein, however are not limited only to vertebral bodies, and may be utilized for treating any bone structure. Such bones may, for example, be in the limbs of the patient, and may include long bones, femurs, pelvic bones, ribs, the skull, or any other bone structure not described herein. The implant can be a pedicle screw when the bone structure is a vertebra. However, other types of implants are contemplated, and the disclosure is not limited solely to pedicle screw preparation. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants, acetabular cup implants, femur stem implants, screws, anchors, other fasteners, and the like. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications.

The system 10 includes a robotic manipulator 14 (hereinafter 'manipulator'). In one example, the manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. In other examples, more than one manipulator 14 may be utilized in a multiple arm configuration. The manipulator 14 comprises a plurality of joints (J) and a plurality of joint encoders 19 located at the joints (J) for determining position data of the joints (J). For simplicity, one joint encoder 19 is illustrated in FIG. 1, although it is to be appreciated that the other joint encoders 19 may be similarly illustrated. The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J). In one example, each of the joints (J) of the manipulator 14 are actively driven. In other examples, some joints (J) may be passively driven while other joints (J) are actively driven.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference point, which does not move in the manipulator coordinate system MNPL. The manipulator 14 and/or manipulator cart 17 house a manipulator computer 26, or other type of control unit.

In some examples, the manipulator 14 can be a hand-held manipulator where the base 16 is a base portion of a tool (e.g., a portion held free-hand by the user and supported exclusively by the user against the force of gravity) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined. Such a manipulator 14 is shown in U.S. Pat. No. 9,707,043, filed on Aug. 31, 2012, entitled, "Surgical Instrument Including Housing, A Cutting Accessory that Extends from the Housing and Actuators that Establish the Position of the Cutting Accessory Relative to the Housing," which is hereby incorporated herein by reference.

A surgical tool 20 (hereinafter 'tool') couples to the manipulator 14 and is movable relative to the base 16 to interact with the anatomy (A). The tool 20 is or forms part of an end effector 22. The end effector 22 may be defined as the unit which attaches to the robotic manipulator 14. In one example, the end effector 22 attaches to a distal joint (J) of the manipulator 14. The tool 20 may be grasped by the operator. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. Descriptions of the end effector 22 herein may apply fully to the tool 20, and vice-versa, depending on the configuration of the end effector 22 and the tool 20.

The tool 20 may include an energy applicator 24 that may be designed to contact or facilitate contact of an object (such as a screw) with the tissue of the patient 12 at the surgical site. In some configurations, the energy applicator 24 is an accessory that can releasably attach to the tool 20. In alternative configurations, the energy applicator 24 is integrated with the tool 20 such that they are part of a common device. For at least this reason, descriptions of the tool 20 herein may apply fully to the energy applicator 24, and vice-versa, depending on the configuration of the tool 20 and energy applicator 24.

Figure 3:
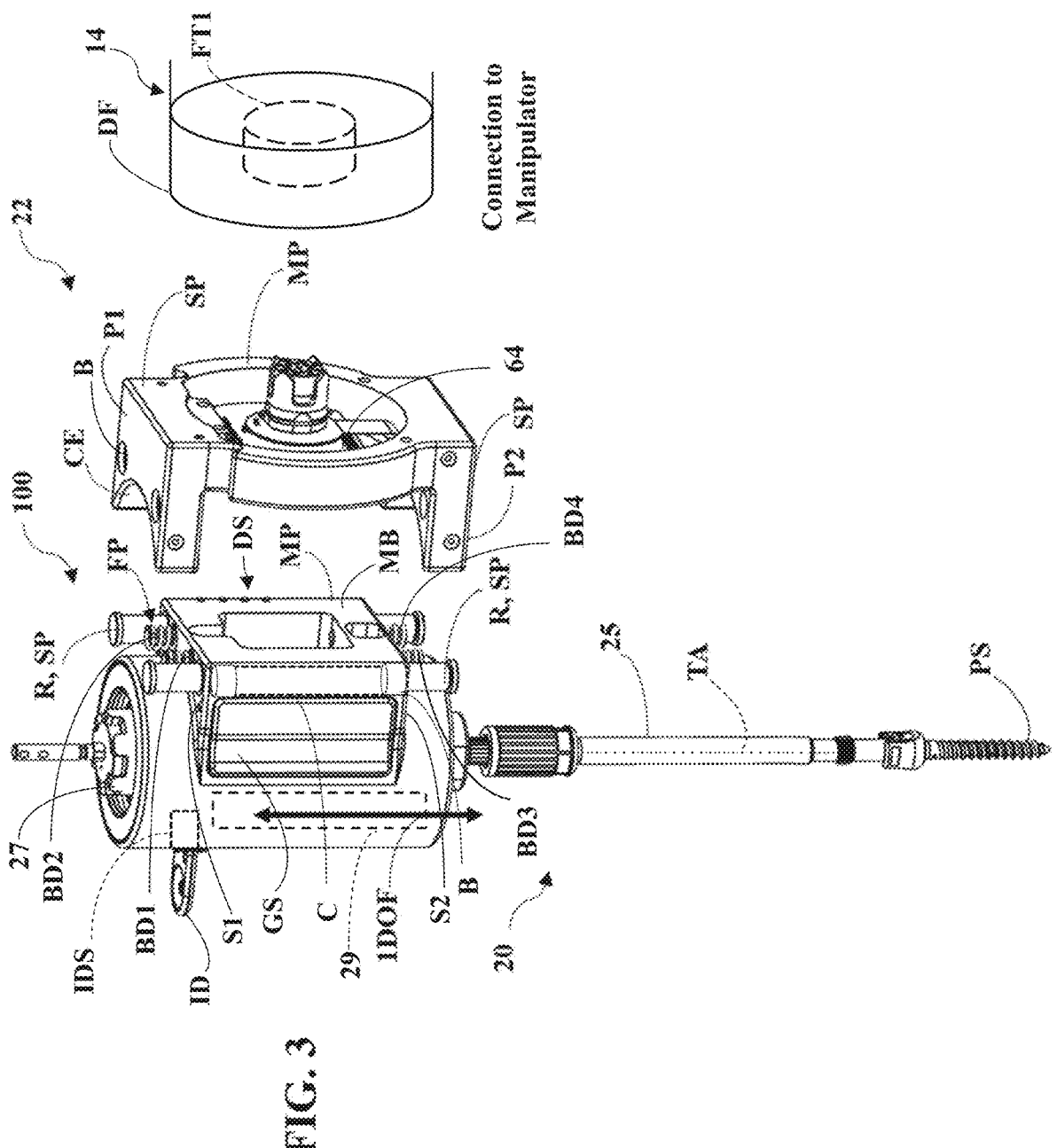
FIG. 3 is a partially exploded perspective view of an assembly comprising an end effector, tool, compliance mechanism and distal flange of the manipulator, according to one implementation.

In one example, the tool 20 is a screwdriver, particularly for driving pedicle screws (PS), for example as shown in FIG. 3. The pedicle screw (PS) may be releasably coupled to the tool 20 according to any suitable manner. The tool 20 may comprise a tool shaft 25 that is disposed along a tool axis (TA) or cutting axis. The tool shaft 25 rotates about the tool axis (TA). In another example, the tool 20 includes a drill bit, such as one adapted to create pilot holes within the anatomy (A). In another example, the tool 20 includes a cutting bur, and more specifically, a rotary cutting bur that may be configured to remove tissue or bone material of the anatomy (A). Alternatively, the tool 20 may include a saw blade, an ultrasonic vibrating tip, or the like.

A proximal end of the tool shaft 25 can be connected to a tool driver 27 that is driven by a tool motor 29, wherein the tool driver 27 and tool motor 29 are optionally included within a body of the end effector 22, as shown in FIG. 3, for example. The tool 20 can include both a low speed and a high-speed tool driver 27 and motor 29 for performing different functions, such as drilling or burring and driving the pedicle screw (PS). A two-stage speed increase can also be provided in the tool 20. The low and high-speed drivers can be located within the body of the end effector 22, as shown in FIG. 3. The manipulator 14 and the tool 20, and components thereof, may be arranged in alternative configurations. The tool 20 can be like that described in U.S. Patent Application Publication No. 2014/0276949, filed on Mar. 15, 2014, entitled, "End Effector of a Surgical Robotic Manipulator," or like that described in U.S. Pat. No. 11,160, 620, entitled "End Effectors And Methods For Driving Tools Guided By Surgical Robotic Systems", the contents of both being hereby incorporated by reference in their entirety.

The tool 20 comprises a tool center point (TCP), which in one example, is a predetermined reference point defined relative to the tool 20. The TCP has known position in its own coordinate system and the manipulator 14 commands positioning of the tool 20 based on the location of the TCP. The TCP may be located at any suitable portion of the tool 20, including at a center of gravity of the tool 20, at any point along the shaft 25, at a distal tip, peripheral portion, proximal portion, or may be located remote from the tool 20 body. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the target site to perform the desired treatment.

Figure 2:
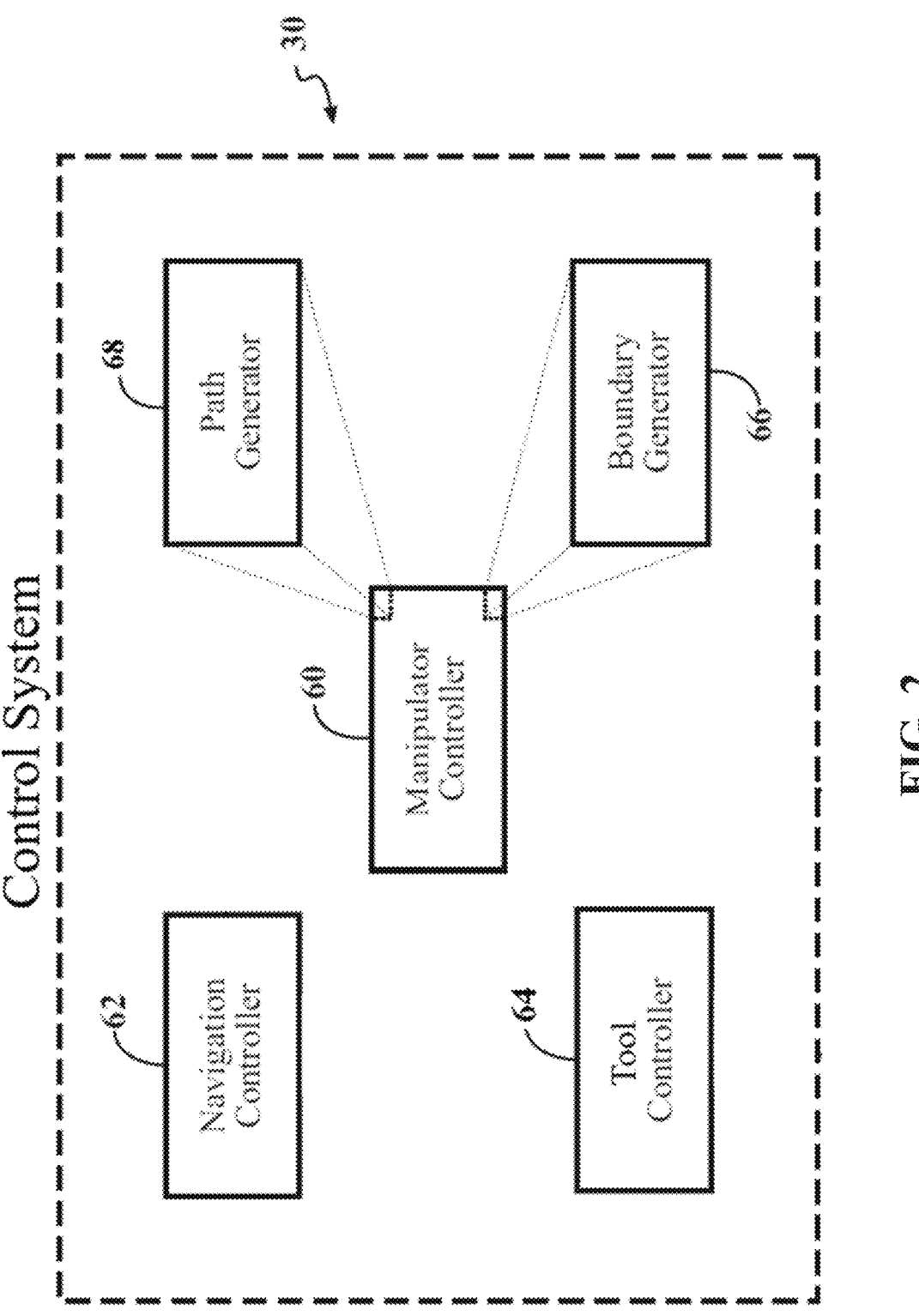
FIG. 2 is a block diagram of a control system that can be used with the surgical system, according to one implementation.

Referring to FIG. 2, the system 10 includes one or more controllers 60, 62, 64 (hereinafter referred to as "control system"). The control system 30 includes software and/or hardware for controlling the manipulator 14. The control system 30 directs the motion of the manipulator 14 and controls a state (position and/or orientation) of the tool 20 with respect to a coordinate system. In one example, the coordinate system is the manipulator coordinate system MNPL, as shown in FIG. 1. The manipulator coordinate system MNPL has an origin located at any suitable pose with respect to the manipulator 14. Axes of the manipulator coordinate system MNPL may be arbitrarily chosen as well. Generally, the origin of the manipulator coordinate system MNPL is defined at the fixed reference point of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

As shown in FIG. 1, the system 10 may further include a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the manipulator 14, the tool 20 and the anatomy (A), e.g., certain vertebrae or the pelvis of the patient. The navigation system 32 tracks these objects to gather state information of one or more of the objects with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 can include a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, head-mounted devices, and the like.

The navigation system 32 is configured to depict a visual representation of the anatomy and the tool 20 for visual guidance of any of the techniques described. The visual representation may be real (camera) images, virtual representations (e.g., computer models), or any combination thereof. The visual representation can be presented on any display viewable to the surgeon, such as the displays 38 of the navigation system 32, head mounted devices, or the like. The representations may be augmented reality, mixed reality, or virtual reality.

The navigation system 32 also includes a navigation localizer 44 (hereinafter "localizer") coupled to the navigation computer 36 and that localizes the states of the tracked objects to a localizer coordinate system LCLZ. In one example, the localizer 44 is an optical localizer and includes a camera unit 46. The camera unit 46 has an outer casing 48 that houses one or more optical sensors 50.

The navigation system 32 may include one or more trackers. In one example, the trackers include a pointer tracker 59, one or more manipulator trackers 52, one or more patient trackers 54, 56. In the illustrated example of FIG. 1, the manipulator tracker 52 is coupled to the tool 20 (i.e., tracker 52A) or the end effector 22, the first patient tracker 54 is coupled to a first bone (e.g., vertebra) of the patient 12, and the second patient tracker 56 is coupled to a second bone (e.g., pelvis) of the patient 12. The pointer tracker 59 is coupled to a pointer P used for registering the anatomy to the localizer coordinate system LCLZ. The manipulator tracker 52 may be affixed to any suitable component of the manipulator 14, in addition to, or other than the tool 20, such as the base 16 (i.e., tracker 52B), or any one or more links 18 of the manipulator 14. Those skilled in the art appreciate that the trackers 52, 54, 56, 59 may be fixed to their respective components in any suitable manner. Furthermore, the patient trackers 54, 56 may have other configurations that do not require implantation to bone. For instance, the patient trackers 54, 56 can be non-invasive skin trackers, ultrasound trackers, electromagnetic trackers, or the like.

When optical localization is utilized, one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of one or more of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the manipulator 14 and the patient 12. The illustrated tracker configuration is provided merely as one example for tracking objects within the operating space. Any number of trackers may be utilized and may be located in positions or on objects other than shown. In other examples, such as described below, the localizer 44 may detect objects absent any trackers affixed to objects.

In one example, the navigation system 32 and/or localizer 44 are ultrasound-based. For example, the navigation system 32 may comprise an ultrasound imaging device coupled to the navigation computer 36. The ultrasound imaging device may be robotically controlled, or may be hand-held. The ultrasound imaging device images any of the aforementioned objects, e.g., the manipulator 14 and the patient 12, and generates state signals to the control system 30 based on the ultrasound images. The ultrasound images may be of any ultrasound imaging modality. The navigation computer 36 may process the images in near real-time to determine states of the objects. Ultrasound tracking can be performed absent the use of trackers affixed to the objects being tracked. The ultrasound imaging device may have any suitable configuration and may be different than the camera unit 46 as shown in FIG. 1. One example of an ultrasound tracking system can be like that described in U.S. patent application Ser. No. 15/999,152, filed Aug. 16, 2018, entitled "Ultrasound Bone Registration With Learning-Based Segmentation And Sound Speed Calibration," the entire contents of which are incorporated by reference herein.

In another example, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the control system 30 based on RF signals received from the RF emitters. The navigation computer 36 and/or the control system 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electromagnetic tracker, inductive tracker, or the like. The trackers may be passive or actively energized. The EM transceiver generates an EM field and generates state signals to the control system 30 based upon EM signals received from the trackers. The navigation computer 36 and/or the control system 30 may analyze the received EM signals to associate relative states thereto. Again, such navigation system 32 examples may have structural configurations that are different than the navigation system 32 configuration as shown throughout the Figures.

In yet another example, the navigation system 32 and/or localizer 44 utilize a machine vision system which includes a video camera coupled to the navigation computer 36. The video camera is configured to locate a physical object in a target space. The physical object has a geometry represented by virtual object data stored by the navigation computer 36. The detected objects may be tools, obstacles, anatomical features, trackers, or the like. The video camera and navigation computer 36 are configured to detect the physical objects using image processing techniques such as pattern, color, or shape recognition, edge detection, pixel analysis, neutral net or deep learning processing, optical character recognition, barcode detection, or the like. The navigation computer 36 can compare the captured images to the virtual object data to identify and track the objects. A tracker may or may not be coupled to the physical object. If trackers are utilized, the machine vision system may also include infrared detectors for tracking the trackers and comparing tracking data to machine vision data. Again, such navigation system 32 examples may have structural configurations that are different than the navigation system 32 configuration as shown throughout the Figures. Examples of machine vision tracking systems can be like that described in U.S. Pat. No. 9,603,665, entitled "Systems and Methods for Establishing Virtual Constraint Boundaries" and/or like that described in U.S. Pat. No. 11,291,507, entitled "Systems and Method for Image Based Registration and Calibration," the entire contents of which are incorporated by reference herein. In some instances, the video camera can be coupled directly to the manipulator 14, such as described in U.S. Pat. No. 10,531, 926, entitled "Systems And Methods For Identifying And Tracking Physical Objects During A Robotic Surgical Procedure", the contents of which are incorporated by reference herein.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

As shown in FIG. 2, the control system 30 includes a manipulator controller 60, a navigation controller 62 and a tool controller 64. The manipulator controller 60 processes data to direct motion of the manipulator 14. In one example, as shown in FIG. 1, the manipulator controller 60 is implemented on the manipulator computer 26. The manipulator controller 60 may receive and process data from a single source or multiple sources. The control system 30 further includes a navigation controller 62 for communicating the state data relating to the anatomy to the manipulator 14 to the manipulator controller 60. The manipulator controller 60 receives and processes the state data provided by the navigation controller 62 to direct movement of the manipulator 14. In one example, as shown in FIG. 1, the navigation controller 62 is implemented on the navigation computer 36. The manipulator controller 60 or navigation controller 62 may also communicate states of the patient 12 and manipulator 14 to the operator by displaying an image of the anatomy and the manipulator 14 on the one or more displays 38. The manipulator computer 26 or navigation computer 36 may also command display of instructions or request information using the display 38 to interact with the operator and for directing the manipulator 14. The tool controller 64 may be implemented by a processor located within the end effector 22 and/or tool 20 body. The tool controller 64 may receive inputs from the user, signals from sensors that detect conditions related to the tool 20 or environment of the tool 20, and/or detect or evaluate operating conditions or performance of the tool 20. The tool controller 64 can communicate information to the manipulator controller 60 such that this information can be utilized to adjust control of the manipulator 14 and/or tool 20.

The one or more controllers 60, 62, 64 may be implemented on any suitable device or devices in the system 10, including, but not limited to, the manipulator computer 26, the navigation computer 36, the end effector 22, and any combination thereof. As will be described herein, the control system 30 is not limited to one controller, but may include a plurality of controllers for various systems, components or sub-systems of the surgical system 10. These controllers may be in communication with each other (e.g., directly or indirectly), and/or with other components of the surgical system 10, such as via physical electrical connections (e.g., a tethered wire harness) and/or via one or more types of wireless communication (e.g., with a WiFi™ network, Bluetooth®, a radio network, and the like). Any of the one or more controllers 60, 62, 64 may be realized as or with various arrangements of computers, processors, control units, and the like, and may comprise discrete components or may be integrated (e.g., sharing hardware, software, inputs, outputs, and the like). Any of the one or more controllers 60, 62, 64 may implement their respective functionality using hardware-only, software-only, or a combination of hardware and software. Examples of hardware include, but is not limited, single or multi-core processors, CPUs, GPUs, integrated circuits, microchips, or ASICs, digital signal processors, microcontrollers, field programmable gate arrays, systems on a chip, discrete circuitry, and/or other suitable hardware, and the like. The one or more controllers 60, 62, 64 may implement software programs, software modules, algorithms, logical rules, look-up tables and other reference data, and various software layers for implementing any of the capabilities described herein. Equivalents of the software and hardware for the one or more controllers 60, 62, 64, and peripheral devices connected thereto, are fully contemplated. The software modules may be part of a computer program or programs that operate on the manipulator computer 26, navigation computer 36, end effector 22, or a combination thereof, to process data to assist with control of the system 10. The software modules include instructions stored in one or more non-transitory computer readable medium or memory on the manipulator computer 26, navigation computer 36, end effector 22, or a combination thereof, to be executed by one or more processors of the computers 26, 36. Additionally, software modules for prompting and/or communicating with the operator may form part of the program or programs and may include instructions stored in memory on any respective component. The operator may interact with the first and second input devices 40, 42 and the one or more displays 38 to communicate with the software modules. The user interface software may run on a separate device from the manipulator computer 26 and navigation computer 36.

As shown in FIG. 2, the control system 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual objects (VO) for constraining the tool 20. Such virtual objects (VO) may also be referred to as virtual meshes, virtual boundaries, virtual constraints, line or plane haptics, or the like. The virtual objects (VO) may be defined with respect to a 3-D bone model registered to the one or more patient trackers 54, 56 such that the virtual objects (VO) are virtually tracked relative to the anatomy (A). The state of the tool 20 can be tracked relative to the virtual objects (VO). In one example, the state of the TCP is measured relative to the virtual objects (VO) for purposes of determining when and where haptic feedback force is applied to the manipulator 14, or more specifically, the tool 20.

One type of virtual object (VO) is a line haptic, as shown in FIGS. 4-12. This line haptic more specifically is a planned trajectory (PT). The planned trajectory (PT) is based on a surgical plan and is defined in relation to an anatomical model of the anatomy (A). The planned trajectory (PT) can be registered to the physical anatomy (A) using the navigation system 34 using any type of registration technique, such as imageless or pointer (P) registration, 2D/3D registration, 3D/3D registration, and the like. Once registered to the anatomy (A), the control system 30 takes the planned trajectory (PT) into account to constrain movement of the tool 20, or the tool shaft 25 to stay on the planned trajectory (PT). The constrained movement can allow movement along the planned trajectory (PT). The tool 20 can exit the planned trajectory (PT) based on user input, switching modes of operation, or detection of user applied forces to pull the tool 20 of the planned trajectory (PT). The above-described line haptics could alternatively be plane haptics for a planned trajectory (PT). The plane haptic can be to constrain the tool 20 to cutting planes and may be particularly useful when the tool 20 comprises a planar saw blade that can be constrained to the cutting plane(s) for performing the distal femur cuts for total knee arthroplasty.

A tool path generator 68 is another software module run by the control system 30, and more specifically, the manipulator controller 60. The tool path generator 68 generates a path for the tool 20 to traverse, such as for removing sections of the anatomy to receive an implant. One exemplary system and method for generating the tool path is explained in U.S. Pat. No. 9,119,655, entitled, "Surgical Manipulator Capable of Controlling a Surgical Instrument in Multiple Modes," the disclosure of which is hereby incorporated by reference. In some examples, the virtual objects (VO) and/or tool paths may be generated offline rather than on the manipulator computer 26 or navigation computer 36. Thereafter, the virtual objects (VO) and/or tool paths may be utilized at runtime by the manipulator controller 60. The planned trajectory (PT) can also be implemented as a tool path that is generated by the tool path generator 68.

The manipulator controller 60 may be an admittance-type controller. In such instances, the manipulator controller 60 receives force as an input and commands position. The manipulator controller 60 is configured to simulate dynamics of the tool 20 in a virtual simulation. The virtual simulation may be based on the tool 20 with or without the energy applicator 24. In one embodiment, the virtual simulation is implemented using a physics engine, which is computer software implemented by the manipulator controller 60 that simulates rigid body dynamics. The virtual simulation may be implemented on a computing device having a non-transitory computer-readable storage medium with an executable program stored thereon. The manipulator controller 60 effectively simulates rigid body dynamics of the tool 20 by virtually applying control forces and/or torques to the virtual rigid body. The control forces and/or torques applied to the virtual rigid body may be user applied. The manipulator 14 may include a force-torque sensor (FT1) that measures these external forces and torques applied to the manipulator 14 and/or tool 20, e.g., in six degrees of freedom (6DOF). Control forces/torques may also be based on other behavior and motion control forces and/or torques. These control forces and/or torques are applied, in part, to control joint (J) position and may be derived from various sources. One of the control forces and/or torques may be a reactive force responsive to interaction of the tool 20 with the virtual boundaries produced by the boundary generator 68. Additionally, control forces and/or torques may be applied to constrain movement of the tool 20 along the tool path provided from the path generator 68. These control forces and/or torques may be applied to constrain orientation of the tool 20 further within an acceptable range of orientations along the tool path. Backdrive control forces indicative of a disturbance along the tool path (e.g., based on external forces applied to the manipulator 14) also may be applied to the virtual rigid body. Control forces and/or torques may be applied to the virtual rigid body to overcome the force of gravity. Other control forces that may applied to the virtual rigid body include, but are not limited to forces to avoid joint limits, forces to avoid singularities between links 18 of the manipulator 14, forces to maintain the tool 20 within a workspace boundary of the manipulator 14, and the like. These various control forces and/or torques to apply to the virtual rigid body are detected and/or determined by the manipulator controller 60 and are inputted into a system of equations that the manipulator controller 60 solves in order to provide a kinematic solution satisfying the system of equations (i.e., satisfying the various control forces and/or torques and any applicable constraints). The manipulator controller 60 may be configured with any suitable algorithmic instructions (e.g., such as an iterative constraint solver) to execute this computation. This operation is performed in the virtual simulation in order to determine the next commanded position of the tool 20 or TCP. The virtual simulation simulates rigid body dynamics of the tool 20 before such dynamics of the tool 20 are physically performed during positioning of the manipulator 14. The virtual rigid body is in a first pose at commencement of each iteration of the virtual simulation. The manipulator controller 60 inputs the control forces and/or torques into the virtual simulation and these control forces and/or torques are applied to the virtual rigid body in the virtual simulation when the virtual rigid body is in the first pose. The virtual rigid body is moved to a subsequent pose having a different state (i.e., position and/or orientation) within Cartesian space in response to the manipulator controller 60 satisfying the inputted control forces and/or torques.

The manipulator 14 may be controlled according to different modes of operation for the system 10. For example, the system 10 may enable the manipulator 14 to interact with the anatomy (A) using manual modes, automated modes, and/or hybrid modes of operation. These modes can be like those described in U.S. Pat. No. 9,119,655, entitled, "Surgical Manipulator Capable of Controlling a Surgical Instrument in Multiple Modes," the disclosure of which is hereby incorporated by reference.

A. Automated Mode

Figures 10, 11, 12:
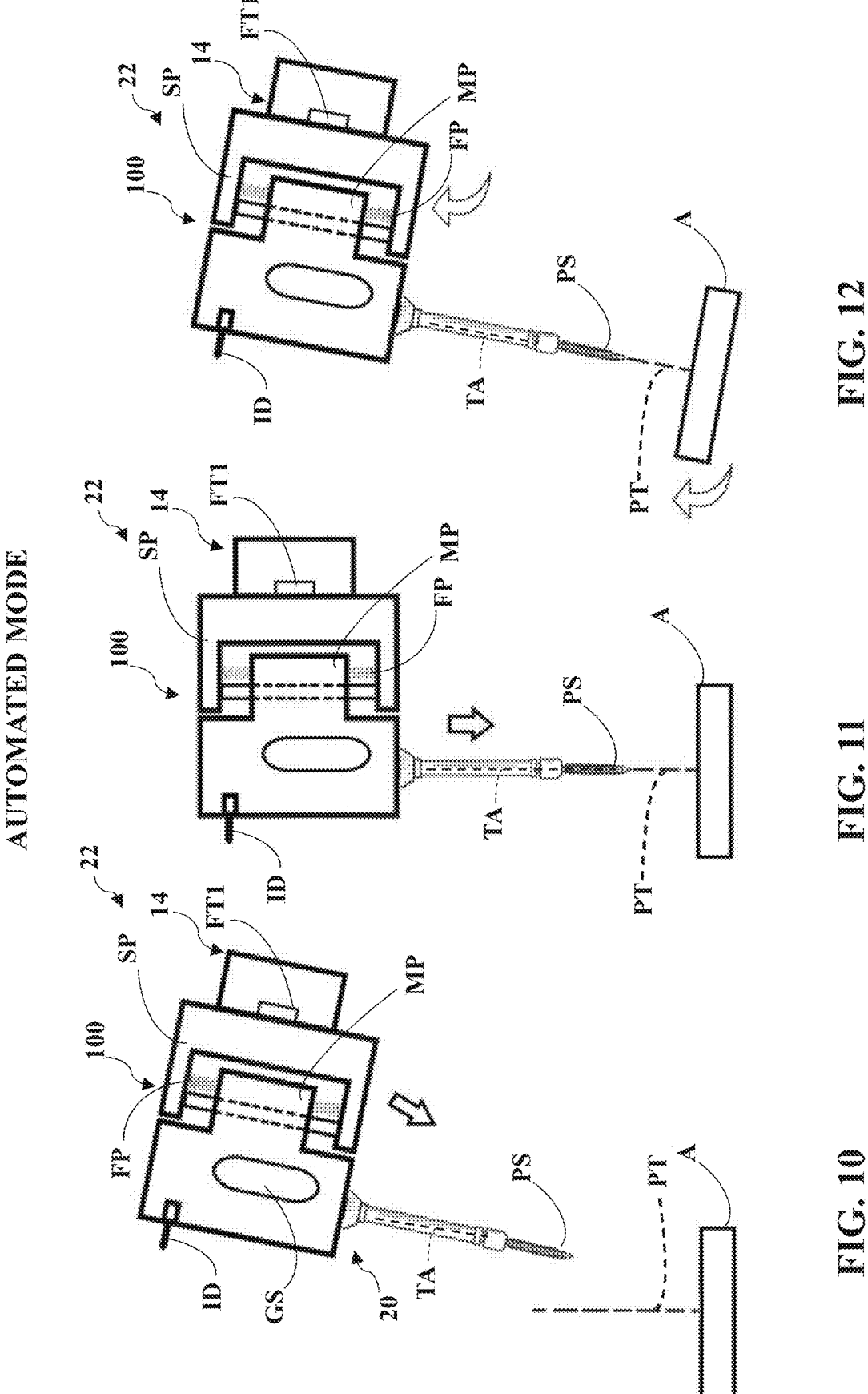
FIG. 10 is an illustration demonstrating operation of the end effector using an automated manual mode whereby the end effector is automatically moved towards the anatomy, according to one implementation.
FIG. 11 is an illustration demonstrating operation of the end effector using the automated manual mode whereby the end effector is automatically moved onto and constrained by the planned trajectory, according to one implementation.
FIG. 12 is an illustration demonstrating operation of the end effector using the automated manual mode whereby the pose of the anatomy changes and the pose of the end effector is automatically updated to maintain the tool on the planned trajectory, according to one implementation.

With reference to FIGS. 10-12, in the automated mode, the manipulator 14 directs movement of the tool 20 relative to the anatomy (A) in an automated manner. In one instance, the control system 30 determines forces and torques to apply to the virtual rigid body to advance and constrain the tool 20 along any trajectory or path in the automated mode. Movement of the tool 20 in the automated mode is constrained in relation to the virtual constraints generated by the boundary generator 66 and/or path generator 68. The manipulator 14 is capable of moving the tool 20 free of user-applied force. In other words, in the automated mode, the user does not physically move the tool 20 by applying external force to move the tool 20. Instead, the user may use some form of control to manage starting and stopping of movement. For example, the operator may hold down a button of a control to start movement of the tool 20 and release the button to stop movement of the tool 20. Alternatively, the operator may press a button to start movement of the tool 20 and press a button to stop motorized movement of the tool 20 along the trajectory or path. The manipulator 14 uses motorized movement to advance the tool 20 in accordance with pre-planned parameters.

FIGS. 10-12 illustrate additional control examples that are possible with the automated mode. In FIG. 10, the control system 30 commands the manipulator 14 in the automated mode to move the end effector 22 and tool 20 from a first position that is off the planned trajectory (PT) to a second position that is on or closer to the planned trajectory (PT). During this automated movement, the manipulator 14 may move the tool 20 directly to the planned trajectory (PT) or to a predefined or threshold distance from the planned trajectory (PT). In FIG. 11, the tool 20 is located on the planned trajectory (PT) such that movement of the shaft 25 is virtually constrained to the planned trajectory (PT). In FIG. 11, the control system 30 commands the manipulator 14 in the automated mode to automatically move the end effector 22 and tool 20 downwards along the planned trajectory (PT) and towards the anatomy (A). During this automated movement along the planned trajectory (PT), the manipulator 14 may move the tool 20 tip or pedicle screw (PS) until contact is made with the anatomy (A) or to a predefined or threshold distance from the anatomy (A). Additionally, the tool 20 or pedicle screw (PS) can be driven into the anatomy (A) using the automated mode. For instance, in the automated mode, the manipulator 14 can automatically advance and rotate the tool 20 according to parameters related to the thread pitch of the pedicle screw (PS), such as described in U.S. Pat. No. 11,033,341, entitled "Robotic Spine Surgery System And Methods" the entire contents of which are hereby incorporated by reference. In FIG. 12, the control system 30 commands the manipulator 14 in the automated mode to automatically maintain the tool 20 on the planned trajectory (PT) such that the tool 20 pose is updated for any changed pose of the anatomy (A) or planned trajectory (PT) in space. Arrows in FIG. 12 illustrate a scenario where the anatomy (A) pose is tilted, causing a corresponding tilt of the planned trajectory (PT). The navigation system 34 can detect this change of the anatomy (A) pose. In response, the manipulator 14 automatically and immediately moves the tool 20 such that the shaft 25 remains aligned to the tilted planned trajectory (PT). This way, unexpected movements of the anatomy (A) do not interfere with the surgical workflow.

In other examples, the control system 30 can control the manipulator 14 in the automated mode to automatically move from one planned trajectory (PT) to another planned trajectory (PT), and so on. At each planned trajectory (PT), the tool 20 can be automatically controlled to drill a hole or install a pedicle screw (PS).

B. Non-Isolated Manual Mode

With reference to FIGS. 6-9, the system 10 may also be operated according to a non-isolated manual mode. Here, the operator physically contacts or grasps the tool 20 or end effector 22 to cause movement of the tool 20. In response, the manipulator 14 controls movement of the tool 20 pursuant to the user movement. The non-isolated manual mode can be implemented as an impedance-based control mode or an admittance-based control mode.

Figures 4, 5:
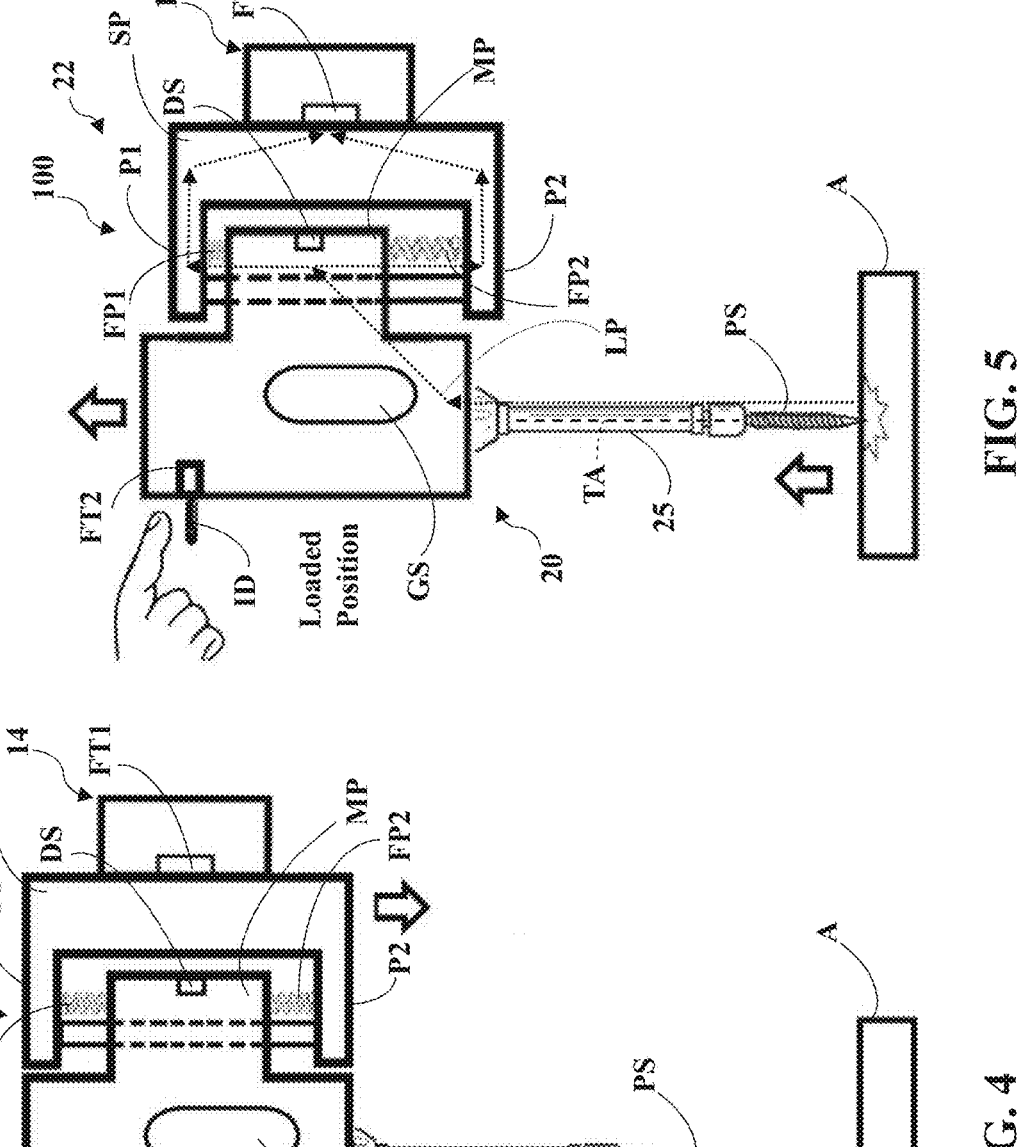
FIG. 4 is an illustration demonstrating operation of the end effector using an isolated manual mode to move the tool towards the anatomy, according to one implementation.
FIG. 5 is an illustration demonstrating operation of the end effector using the isolated manual mode whereby the compliance mechanism enables compliant motion of the tool in response to external force being applied to the tool by the anatomy, according to one implementation.

When admittance-based, the manipulator 14 monitors the forces and torques placed on the tool 20 by the operator in order to position the tool 20. The phrase "non-isolated" is used to describe this manual mode because forces/torques applied to the tool 20 by the anatomy (A) can directly reach the force/torque sensor (FT1) based on the load path (LP) as depicted in FIG. 5. The load path (LP) starts from the anatomy (A) and will pass respectively through the tool shaft 25, and other components until the load path (LP) terminates at the manipulator force/torque sensor (FT1). Hence, the force/torque sensor (FT1) is not mechanically isolated from the external forces/torques applied to the tool 20. Furthermore, the measured forces/torques are computationally "non-isolated" because they are utilized in the virtual simulation to determine the next commanded position of the tool 20. The force/torque sensor (FT1) measures these external forces and torques applied to the manipulator 14, end effector 22 and/or tool 20, e.g., in 6DOF. In one example, the force/torque sensor (FT1) is coupled between the distal-most link of the manipulator (J6) and the end effector 22. The force/torque sensor (FT1) may comprise deformable members, such as beams or hoops, which undergo tension or compression pursuant to the load. Strain gauges, or load cells, may measure the deformation and send signals to the control system 30. The force/torque sensor (FT1) physically supports the end effector 22 and tool 20 against the force of gravity and during movement of the manipulator 14. Hence, the force/torque sensor (FT1) is designed to be stiff, while allowing only limited deformation, to ensure predictability of the TCP location for stable robotic control. In one example, the force/torque sensor (FT1) deforms no more than 1 mm in any direction. One example of the force/torque sensor (FT1) can be like that described in U.S. Pat. No. 9,993,309 entitled "Force/Torque Transducer and Method of Operating the Same", the contents of which are hereby incorporated by reference in their entirety. In response to the applied forces and torques, the control system 30 is configured to determine a commanded position of the tool 20 by evaluating the user-applied forces/torques with respect to virtual model of the tool 20 in the virtual simulation. The manipulator 14 then mechanically moves the tool 20 to the commanded position in a manner that emulates the movement that would have occurred based on the forces and torques applied externally by the user. The emulated movement can be 1DOF, or up to 6DOF, movement of the manipulator 14. Movement of the tool 20 in the non-isolated manual mode can also be constrained in relation to the virtual constraints generated by the boundary generator 66 and/or path generator 68, including the planned trajectory (PT).

As shown throughout FIGS. 3-12, the tool 20 or end effector 22 can comprise a grip sensor (GS) to enable the user to manually control the manipulator 14 in the non-isolated manual mode. The grip sensor (GS) can be coupled to, or integrated in, the body of the end effector 22 or tool 20. The grip sensor (GS) can be a moveable, tactile interface (e.g., pivoting button) or a digital (non-moving) interface. The grip sensor (GS) may also be a separate component, such as on a cable-connected or wireless pendant.

In the example shown, the grip sensor (GS) comprises two separate buttons that are located on opposing sides of the body of the tool 20. The buttons are positioned so that one button can be grasped by four fingers of the user while the opposing button can be grasped by the thumb of the user. Once the control system 30 detects that both buttons of the grip sensor (GS) are grasped or depressed, the control system 30 can activate the non-isolated manual mode or continue enabling the user to operate the manipulator 14 in the non-isolated manual mode so long as the grip sensor (GS) input is detected. Hence, this dual-button configuration may be provided to ensure the user's intention and to avoid inadvertent activation of a single button. In other implementations, the grip sensor (GS) has only one button or trigger to be grasped.

Figures 6, 7:
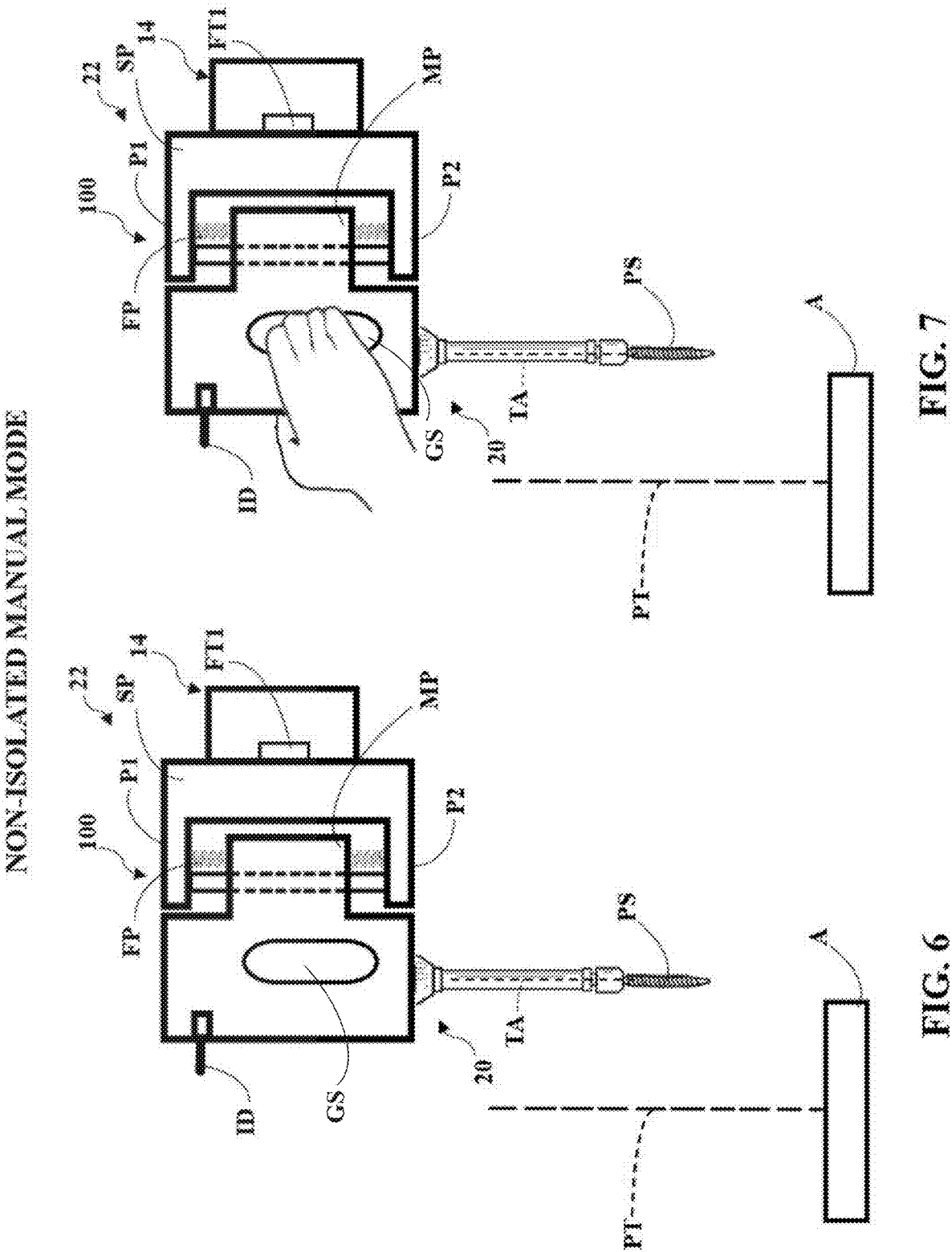
FIG. 6 is an illustration demonstrating operation of the end effector using a non-isolated manual mode whereby the end effector is in a stationary pose, according to one implementation.
FIG. 7 is an illustration demonstrating operation of the end effector using the non-isolated manual mode whereby the user actuates a grip sensor on the end effector to apply forces/torques to control the manipulator, according to one implementation.
Figures 8, 9:
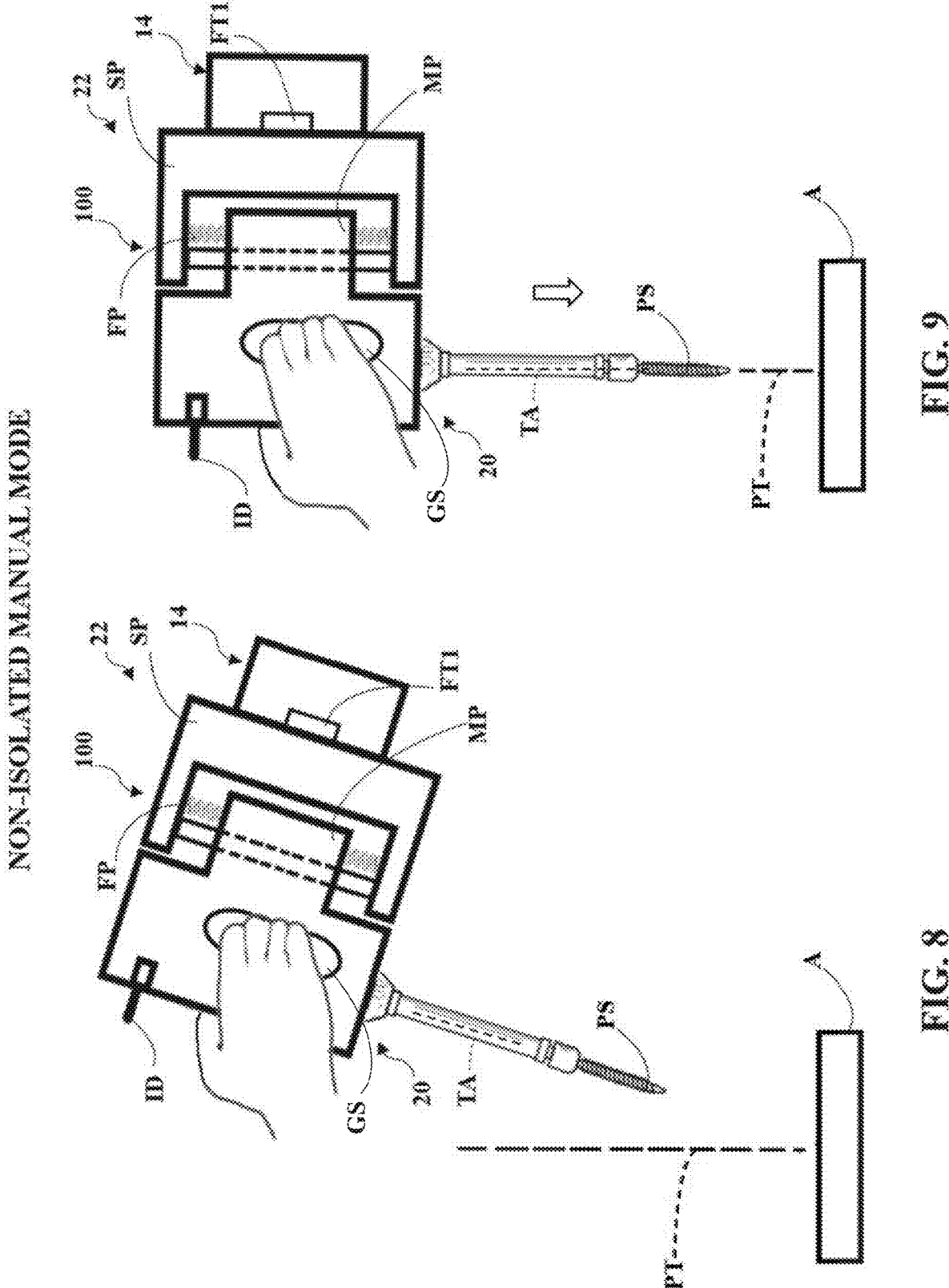
FIG. 8 is an illustration demonstrating operation of the end effector using the non-isolated manual mode whereby the user continues to actuate the grip sensor on the end effector to apply forces/torques to orient the tool towards a planned trajectory, according to one implementation.
FIG. 9 is an illustration demonstrating operation of the end effector using the non-isolated manual mode whereby the user continues to actuate the grip sensor on the end effector to apply forces/torques to move the tool towards the anatomy as the tool is constrained by planned trajectory, according to one implementation.

FIGS. 6-9 illustrate additional control examples that are possible with the non-isolated manual mode. In FIG. 6, the end effector 22 and tool 20 are located at a first position that is off the planned trajectory (PT) and the manipulator 14 may be controlled in any mode or may be paused or disabled at this location. In FIG. 7, the control system 30 detects that the user has grasped the grip sensor (GS). In turn, the control system 30 activates the non-isolated manual mode. In FIG. 8, the user, while grasping the grip sensor (GS), applies forces/torques to the tool 20 and/or end effector 22. The applied forces/torques are detected by the force/torque sensor (FT1) at the distal flange of the manipulator 14. The control system 30, using these force/torque readings, commands the pose (position and/or orientation) of the tool 20 and/or end effector 22 to emulate the user's applied forces/torques. In the example shown, the control system commands the manipulator 14 in the non-isolated manual mode to move and orient the tool 20 and/or end effector 22 from a first position (of FIGS. 6 and 7) towards the anatomy (A), and more specifically to a second pose that is on or closer to the planned trajectory (PT) as shown in FIG. 8. During this movement, the user may apply forces/torques to cause the manipulator 14 to move the tool 20 directly to the planned trajectory (PT) or to a predefined or threshold distance from the planned trajectory (PT). In FIG. 9, the tool 20 is located on the planned trajectory (PT) such that movement of the shaft 25 is virtually constrained to the planned trajectory (PT) in the non-isolated manual mode. In FIG. 9, the user applies downward forces/torques to the tool 20 and/or end effector 22 to move towards the anatomy (A) and the applied forces/torques are again detected by the force/torque sensor (FT1). The control system 30, using the force/torque readings, commands the manipulator 14 in the non-isolated manual mode to move the end effector 22 and/or tool 20 downwards along the planned trajectory (PT) and towards the anatomy (A) thereby emulating the user's applied forces/torques. Along the planned trajectory (PT), the user may apply forces/torques to cause the manipulator 14 to move the tool 20 tip or pedicle screw (PS) until contact is made with the anatomy (A) or to a predefined or threshold distance from the anatomy (A). Additionally, the tool 20 or pedicle screw (PS) can be driven into the anatomy (A) using the non-isolated manual mode. For instance, in the non-isolated manual mode, the manipulator 14 can automatically advance or rotate the tool 20 according to parameters related to the thread pitch of the pedicle screw (PS). In one scenario, the user applies forces to advance the tool 20 and the tool 20 is controlled to automatically rotate the tool 20 according to the thread pitch of the pedicle screw (PS). In another scenario, the user applies can actuate a switch to rotate the tool 20, and the manipulator 14 is controlled to automatically advance the tool 20 according to the thread pitch of the pedicle screw (PS). Thread pitch control can be like that described in U.S. Pat. No. 11,033,341, entitled "Robotic Spine Surgery System And Methods" the entire contents of which are hereby incorporated by reference.

In other examples, the user can apply forces/torques in the non-isolate manual mode to cause the control system 30 to move the end effector 22 and/or tool 20 from one planned trajectory (PT) to another planned trajectory (PT), and so on. At each planned trajectory (PT), the use can apply forces/torques to the tool 20 to drill a hole or install a pedicle screw (PS). In other examples, the grip sensor (GS) can be used to reorient the tool 20 or override control during operation in any mode.

II. Compliance Mechanism and Robotic Techniques Involving the Same

Described in this section, and with further reference to FIGS. 3-13, are systems, methods, end effectors, and techniques that involve a compliance mechanism 100. The compliance mechanism 100 is part of the system 10 and more specifically, is coupled to the manipulator 14. The compliance mechanism 100 supports the tool 20 and is configured to enable the tool 20 to move, or displace, relative to the manipulator 14 in response to external forces/torques applied to the tool 20. These external forces/torques may be a result of "hard contact" on the tool 20. In some, but not all scenarios, the external forces/torques are applied to the tool 20 by contact between the tool 20 and the anatomy (A), such as a bone. However, the external forces/torques can be applied between the tool 20 and any stiff object, such as another surgical object or tool, such as a retractor or tracker body, or any other stiff part of the anatomy besides bone. In other examples, the external forces/torques may be a result of the anatomy (A) pulling down on the tool 20 after the tool 20 has engaged the anatomy (A) and is being controlled to be released from the anatomy (A), but there is an error involved with such release. Hence, the external forces/torques can either push or pull the tool 20 to cause the displacement. These conditions are often, but not always, error conditions.

The compliance mechanism 100 is provided to absorb displacement of the surgical 20 in response to such external forces/torques. This feature is advantageous for the manipulator 14 which, in one implementation, is an admittance-control system that utilizes the force/torque sensor (FT1) at the distal flange of manipulator 14 to receive an input force/torque for commanding the position of the tool 20. The manipulator 14 may move the tool 20 to a commanded position, and in so doing, the tool 20 may abruptly contact the stiff object or improperly engage the anatomy (A) due to circumstances unforeseen by the control system 30. This issue is particularly relevant where the tool 20 is used to drive an implant, such as a pedicle screw, into a vertebral body. In turn, the physical reactive force occurring due to such abrupt contact or improper engagement may cause a displacement of the tool 20. The compliance mechanism 100 absorbs the displacement of the tool 20 and mechanically dampens the external force/torque such that the force/torque sensor (FT1) at the distal flange of the manipulator 14 is less susceptible to force readings that are derived from these displacement conditions. Furthermore, the compliance mechanism 100 provides sufficient elasticity to absorb the displacement, whereas the force/torque sensor (FT1), alone, is not configured to absorb the displacement due to its overly stiff configuration required for admittance control and robotic stability requirements. As a result, the compliance mechanism 100 resolves the displacement condition such that the manipulator 14 can subsequently command the tool 20 in a stable, predictable, and optimal manner. The compliance mechanism 100 also reduces mechanical impedance of the manipulator 14. Additionally, by accumulating displacement, the compliance mechanism 100 can increase accuracy to determining the position of the TCP of the tool 20. Moreover, the compliance mechanism 100 provides greater functionality for the manipulator 14 by enabling additional modes of operation and workflow capabilities.

Aspects of the compliance mechanism, including methods of using the same, are described in detail below.

A. Compliance Mechanism Aspects and Configuration(s)

1. Relation to Manipulator

The compliance mechanism 100 is configured to be located between the tool 20 and the manipulator 14. In some implementations, the compliance mechanism 100 is coupled between the manipulator 14 and the end effector 22 and/or the tool 20. The compliance mechanism 100 can be a separate portion that is attachable to the manipulator 14, end effector 22 and/or tool 20. In other implementations, such as that shown in FIG. 3, the compliance mechanism 100 is a sub-system of the end effector 22. The end effector 22, including the compliance mechanism 100, can be fixed to the manipulator 14 (e.g., during factory assembly) or releasably coupled to the manipulator 14 (e.g., in the operating room).

The end effector 22, including the compliance mechanism 100 may be releasably attached to, and released from a distal flange (DF) of the manipulator 14 by a mounting system. The mounting system can be like that described in United States Patent App. Pub. No. US20200170724, entitled "Mounting System With Sterile Barrier Assembly For Use In Coupling Surgical Components", the contents of which are hereby incorporated by reference. More specifically, the mounting system may include a first mounting portion (MP) coupled to the end effector 22 and a second mounting portion (MP2) associated with the distal flange (DF) of the manipulator 14. A sterile barrier or drape may be coupled to either mounting portion or may be coupled to a sterile barrier assembly located between the mounting portions. The first mounting portion (MP) or second mounting portion (MP2) may include tensioner movable between a first position and a second position. A plurality of kinematic couplers are configured to engage the mounting portions and are arranged to provide a kinematic coupling between the mounting portions through the sterile barrier assembly to constrain six degrees of freedom of movement between the end effector 22 and the distal flange (DF) when the tensioner is moved to the second position. The first mounting portion (MP) may comprise a plurality of contact surfaces for engaging the plurality of kinematic couplers of the sterile barrier assembly. The first mounting portion (MP) may further comprise a loading mechanism configured to apply a preload force to the second mounting portion through the sterile barrier assembly upon movement of the tensioner from the first position to the second position. Electrical terminals may pass through the first mounting portion (MP) from the manipulator 14 to energize components, such as sensors or motors, associated with the end effector 22 and/or compliance mechanism 100.

2. Mechanical Construction

Implementations of the compliance mechanism 100 are illustrated in FIGS. 3 to 13. The compliance mechanism 100. The compliance mechanism 100 includes a stationary portion (SP) that is coupled or attachable to the robotic manipulator 14, a moveable portion (MP) coupled or attachable to the tool 20, and a flexible portion (FP) disposed between the stationary portion (SP) and the moveable portion (MP).

The stationary portion (SP) is stationary with respect to the moveable portion (MP) but not necessarily always stationary in the robotic workspace. That is, the stationary portion (SP) will move with movement of the distal flange of the manipulator 14. The moveable portion (MP) is configured to move relative to the stationary portion (SP). This movement can be defined in any one or more directions. In one example, the moveable portion (MP) is configured to move relative to the stationary portion (SP) according to 1 degree-of freedom (DOF). The 1DOF movement can be axial or linear (e.g., up/down, left/right) or rotational (e.g., clockwise/clockwise. In the example of FIG. 3, the moveable portion (MP) is configured to displace in a 1DOF linear direction shown by the arrow (1DOF). In one example, the 1DOF linear movement is designed to be parallel to, or coincident to the tool axis (TA) defined along the shaft 25 of the tool 20. In this case, the moveable portion (MP) supports the tool 20, which is a screwdriver for driving the pedicle screw (PS). As the moveable portion (MP) displaces relative to the stationary portion (SP), the tool 20, tool shaft 25, and pedicle screw PS will correspondingly displace by the same amount. In other instances, the moveable portion (MP) can be configured move relative to the stationary portion (SP) according to more than one DOF and up to 6DOF.

In one implementation, the stationary portion (SP) comprises a first (upper) platform (P1) and a second (lower) platform (P2) opposite the first platform (P1). The platforms (P1, P2) can be coupled to, or integrally formed from, a body that is shared by the mounting portion (MP) that couples to the manipulator 14. The platforms (P1, P2) can extend in a direction towards the tool 20 and can define a contoured edge (CE) shaped to receive, and enable relative movement of, the moveable portion (MP) and/or the tool 20. For example, the tool 20 may comprise a barrel shape (as shown) and the contoured edge (CE) can be concave-shaped to correspond to the exterior contour of the barrel. The stationary portion (SP) comprises at least one rail (R) extending between the platforms (P1, P2). In FIG. 3, there are two rails (R) that are orientated parallel to one another and oriented in a direction that is parallel to the tool axis (TA). To secure the rail(s) to the stationary portion (SP), the rail(s) (R) can be disposed in and secured to bores (B) located within each platform (P1, P2). Alternatively, the rail(s) (R) can terminate at, and be coupled to, the interior surface of each platform (P1, P2). As will be described below, the rail(s) (R) helps ensure 1DOF linear movement of the moveable portion (MP). In other examples, the stationary portion (SP) may include any number of rails (R) and these rails (R) may be straight, curved, or curvilinear (e.g., for greater than 1DOF). The rails (R) can have any suitable cross-sectional shape, such as circular (as shown), rectangular, or the like. In some examples, the stationary portion (SP) may include only a single platform (P1, P2) and the rail(s) (R) can extend from the single platform and terminate with a stopper located on the rail(s) (R) and without extending to an opposing platform.

In one implementation, the moveable portion (MP) comprises a body (MB) that is fixed or integrally formed with the body of the tool 20. In other instances, the body (MB) may be coupled to the tool 20 but separately connected thereto, i.e., not integrally formed. The body (MB) of the moveable portion (MP) can include a first (upper) surface (S1) and a second (lower) surface (S2) and the body defines a channel (C) that extends from the first surface (S1) to the second surface (S2). The channel (C) is shaped to receive the corresponding shape of the rail (s) (R) of the stationary portion (SP). The rail (R) is disposed through the channel (C) and the moveable portion (MP) is configured to slide along the rail (R). The body (MB) of the moveable portion (MP) that defines the channel (C) fits within the region between the platforms (P1, P2) of the stationary portion (SP). Bushings (B) may be disposed within the channel (C) to surround the rail (R) and provide a smooth and steady sliding of the rail (R) within the channel (C). The bushings (B) can be fixed to the body (MB) of the moveable portion (MP) and located adjacent to, or between, the first surface (S1) and the second surface (S2).

The flexible portion (FP) is disposed between the stationary portion (SP) and the moveable portion (MP). The flexible portion (FP) can be coupled to either the stationary portion (SP) or the moveable portion (MP) or may be coupled to both stationary and moveable portions. In other instances, the flexible portion (FP) can be disposed between the stationary portion (SP) and the moveable portion (MP) but not necessary connected to either of the stationary or moveable portions. The flexible portion (FP) can be supported by another part of the end effector 22 and in a spaced (floating) relationship to both stationary and moveable portions.

In one implementation, the flexible portion (FP) comprises a biasing device (BD). The biasing device (BD) may comprise any one or more of the following: a spring, such as a compression spring, extension spring, leaf spring, helical spring, torsion spring, Belleville spring or washer, a series-elastic spring, or the like; a gas spring, such as a pull-type, a push-type, a gas damper, gas strut, gas shock; a deformable or elastic member or material, such as an elastic band, elastomeric materials such as rubber, elastic padding or cushioning, or the like. The compliance mechanism 100 can include any number of flexible portions (FP). When more than one flexible portion (FP) is utilized, the flexible portions (FP) may be different types and/or may exhibit different biasing or elastic properties from one another.

In the example, as shown in FIG. 3, the flexible portion (FP) comprises four biasing devices (BD), such as coil springs, and more specifically four compression springs. A first pair of springs (BD1, BD2) are coupled, at one end, to the first surface (S1) of the moveable portion body (MB) and coupled, at the opposing end, to the interior surface of the first platform (P1). The first pair of springs (BD1, BD2) are spaced apart from one another and located between the rails (R). Alternatively, each spring can be positioned to surround one of the rails (R) or can be spaced apart from the rails (R) at a different location from what is shown. Also, each spring can be coupled to only one surface and moveably spaced apart from the other. The first pair of springs (BD1, BD2) can comprise a similar spring constant. A second pair of springs (BD3, BD4) are coupled, at one end, to the second surface (S2) of the moveable portion body (MB) and coupled, at the opposing end, to the interior surface of the second platform (P2). The second pair of springs (BD3, BD4) are spaced apart from one another and located between the rails (R), and parallel to the first pair of springs (BD1, BD2). The second pair of springs (BD3, BD4) can comprise a similar spring constant to each other, and optionally, similar to the first pair.

In one implementation, the first and second pairs of springs (BD1-BD4) can provide the compliance mechanism 100 with a self-centering or a self-neutralizing configuration. That is, each pair of compression springs will bias the moveable portion (MP) from towards a neutral (e.g., unloaded or centered) position in the absence of external forces/torques applied to the tool 20. When a load is applied, one pair of springs will compress and the opposing pair will extend (or undergo tension). In response to external forces/torques no longer being applied to the tool 20, the springs will bias the moveable portion (MP) back to the neutral position. In the neutral position, the flexible portion (FP) may be biased (e.g., undergoing load) or unbiased (not experiencing any load) depending on the configuration of the biasing device(s) (BD). Furthermore, the neutral position may be, but is not necessarily required to be, a position wherein the moveable portion (MP) is centered, or equidistant from opposing reference points relative to the stationary portion (SP). That is, the neutral position may be deliberately designed to be shifted off-center, for example, where greater room for displacement may be desired. Additionally, the loaded position may be, but is not necessarily required to be, a single position. The loaded position could be a range of any number of discrete or continuous positions and can be any position that is other than the neutral position due to the variability of displacement.

In other instances, only one biasing device (BD), or one pair of springs, can be utilized to accomplish movement to the neutral position. For example, the single biasing device (BD) or single pair of springs can be located above or below the moveable portion (MP). This may provide movement to the neutral position based on the understanding that the load may only be applied to the tool 20 from below the tool 20 based on surgical workflow considerations. When located above the moveable portion (MP), the single biasing device (BD) or single pair of springs can push the moveable portion (MP) back to the neutral position after the load is released. When located below the moveable portion (MP), the single biasing device (BD) or single pair of springs can pull the moveable portion (MP) back to the neutral position after the load is released. In these situations, the neutral position can be center, or off center depending on the configuration of the biasing device (BD)

The flexible portion (FP) may be resilient enough to enable the described compliance, but stiff enough to ensure that the moveable portion (MP) remains in the neutral position when no external forces/torques are applied to the tool 20. For example, assuming there is no external force/torque, the flexible portion (FP) may maintain the moveable portion (MP) in the neutral position during movement of the manipulator 14 or against the force of gravity to provide for predictable positioning of the tool 20 relative to the manipulator 14.

3. Compliant Motion

FIGS. 4 and 5 illustrate movement of the compliance mechanism 100 according to one example. In FIG. 4, the manipulator 14 positions the tool 20 such that the tool 20 is spaced away from the anatomy (A), and hence, there is no external force occurring between the tool 20 and the anatomy. Here, the flexible portion (FP) biases the moveable portion (MP) to maintain the moveable portion (MP) in the neutral position. In this example, an upper flexible portion (FP1) and lower flexible portion (FP2) self-center the moveable portion (MP) in the neutral position. In FIG. 4, a downward arrow is shown adjacent to the stationary portion (SP) to illustrate that the manipulator 14 is in the process of moving the end effector 22, including the compliance mechanism 100, downward and towards the anatomy (A).

In FIG. 5, the manipulator 14 moves the end effector 22, including the compliance mechanism 100 downwards and the tool 20 physically contacts the anatomy (A). In this example, the pedicle screw PS is the first object to physically contact the anatomy (A). However, as described, the techniques herein are not limited to use with pedicle screws (PS), and hence, it is contemplated that the tool 20 could be the first point of contact. When pedicle screws (PS) are held by the tool 20, as shown, it should be understood that the pedicle screw (PS) forms part of the tool 20. This hard contact may occur from may conditions which may be error, unexpected, or expected conditions. The hard contact may occur from improper or inadvertent engagement of the tool 20 with the anatomy (A), skiving of the tool 20, accidental contact between the tool 20 and the anatomy (A), improper releasing of the tool 20 from within the anatomy (A), or the like. In the example of FIG. 5, the hard contact occurs because the pedicle screw (PS) did not properly thread into the anatomy (A) during driving of the pedicle screw (PS) by the tool 20. As a result, external forces/torques are applied to the tool 20. This external force causes the moveable portion (MP) and tool 20 to experience an upward displacement relative to the stationary portion (SP). Here, the upper flexible portion (FP1) is compressed and the lower flexible portion (FP2) is extended (or tensioned) to enable the displacement to occur. Based on the example compliance mechanism 100 configuration, the displacement is a linear 1DOF displacement that occurs in a direction that is parallel to the tool axis (TA). Because the contact occurs from below the tool 20, the direction is an upward direction. The tool 20 and moveable portion (MP) are then moved from the neutral position to the loaded position.

After the compliance mechanism 100 enables displacement of the tool 20 and moveable portion (MP), the external force/torque from the anatomy (A) is eliminated or mitigated. In turn, elimination or mitigation of the external force causes the moveable portion (MP) and tool 20 to experience an opposing (downward) return displacement relative to the stationary portion (SP). The upper flexible portion (FP1) releases compression (or undergoes tension) and the lower flexible portion (FP1) releases extension (or undergoes compression) to enable the return displacement to occur. Again, the return displacement is a linear 1DOF displacement that occurs in a direction that is parallel to the tool axis (TA). Because the removal of the contact occurs from below the tool 20, the return direction is a downward direction. The tool 20 and moveable portion (MP) are then moved from the loaded position (shown in FIG. 4) back to the neutral position, as shown in FIG. 4, for example.

The amount of allowed displacement of the compliance mechanism 100 can be designed based on several factors, such as, but not limited to: tool geometry, implant geometry, anatomy geometry, type of surgery, step of surgery, robotic workspace constraints, surgical tool constraints, robot stability requirements, navigation system requirements, surgeon preferences, and the like. Depending on the factors described, the amount of allowed displacement can be any suitable value or range, such as but not limited to: 3 mm-10 mm, 5 mm-20 mm, 10 mm-100 mm, or any value within these ranges.

In some instances, the compliance mechanism 100 can include a manually adjustable stopper that is located between the moveable portion (MP) and the stationary portion (SP) to selectively adjust the amount of allowed displacement. The stopper can move up/down with adjustments to limit movement of the moveable portion (MP). In other instances, stoppers of different sizes can be selectively inserted into the compliance mechanism 100 to provide the desired movement limiting effect. In other instances, a locking mechanism can be coupled to the compliance mechanism 100 to selectively lock the compliance mechanism 100, and in effect, the moveable portion (MP) in a designated position. The locking mechanism can include an actuator that can be manually or electrically activated. A user input, located on the end effector 22, or elsewhere, can be coupled to the locking mechanism to trigger the actuator. The locking mechanism can perform locking in various manners. In one example, the locking mechanism uses the actuator to clasp the rail(s) (R) above and below the surfaces (S1, S2) of the moveable portion body (MB) to lock the moveable portion (MP) relative to the rail(s). In another example, where controlled flexible portion (FP) components are utilized, the locking mechanism can control the flexible portion (FP) to be stationary. In another example, the locking mechanism can use the actuator to variably extend a plunger to touch the interior surfaces of the platforms (P1, P2) of the stationary portion (SP). The locking mechanism can then lock the plunger after its extended. The plunger, in one example, can extend from above and below the surfaces (S1, S2) of the moveable portion body (MB).

The above-described complaint motion can be utilized in many forms. In some scenarios, the complaint motion is used alone, as a passive function, to provide compliance when external forces/torques are applied to the tool 20. In other scenarios, as will be described below, the compliant motion can be used in conjunction with different robotic control schemes.

4. Compliant Mechanism Sensor

The compliance mechanism 100, or end effector 22, may include one or more sensor(s) (DS) that are configured to measure the movement and/or displacement of the tool 20 relative to the manipulator 14, or vice versa, when such movement or displacement is enabled by the compliance mechanism 100. Alternatively, or additionally, the sensor (DS) can measure the movement and/or displacement of the moveable portion (MP) relative to the stationary portion (SP). The sensor (DS) can be coupled to the moveable portion (MP), stationary portion (SP), flexible portion (FP) or any combination thereof. The sensor (DS) can measure movement and/or displacement by measuring any one or more of the following: position, velocity, acceleration, inertia, trajectory, or the like.

One example of the sensor (DS) is shown in FIG. 3. Here, the sensor (DS) comprises magnetic elements (e.g., traces or coils shown in cross-section). The magnetic elements are located within the body (MB) of the moveable portion (MP) and are disposed adjacent to the rail (R). The magnetic elements measure linear position of the rail (R) as the rail (R) moves to different position within the channel (C). Hence, the magnetic elements measure the position of the moveable portion (MP) relative to the stationary portion (SP), or vice-versa. In one implementation, the sensor (DS) is implemented as Hall effect sensor or Hall effect magnetic sensor to sense position of the rail (R) using a magnetic field. The magnetic field may be provided by a permanent magnet attached to, or intrinsically part of, the rail (R). The magnetic field can also be actively generated by the magnetic elements of the sensor (DS) whereby this magnetic field is passed through the rail (R) which comprises a conductive or semi-conductive material. In another implementation, sensor (DS) is implemented as a linear variable differential transformer (LVDT) whereby the sensor (DS) measures displacement by associating a specific signal value for any given position of the rail (R) through electromagnetic coupling of an AC excitation signal on a primary winding of the core and back to the secondary windings. The sensor (DS) can be any suitable type of sensor, such as, but not limited to: a magnetic, electro-magnetic, Hall effect, LVDT, magneto-elastic, magneto-resistive, inductive, capacitive, position encoder, piezo-electric transducer, laser, optical, potentiometer, ultrasonic, inertial, accelerometer, gyroscope, force, strain gauge, image sensor, infrared sensor, or the like.

Measurements from the sensor (DS) can be transmitted to a PCB of the tool controller 64, which can be located anywhere in the body of the end effector 22, tool 20, or compliance mechanism 100. These measurements can be analyzed by the tool controller 64 and/or sent to the control system 30 such that the other controllers are made aware of the measured movement and/or displacement of the tool 20 relative to the manipulator 14. In one example, the measurements from the sensor (DS) are used to determine the position of the TCP. The position of the TCP can be determined for any given state of the compliance mechanism 100, where such position may otherwise be unknown to the control system 30 without the sensor (DS). In other words, the sensor (DS) enables the state of the TCP to be known when error conditions occur due to the external forces/torques being applied to the tool 20. Although the force/torque sensor (FT1) at the distal flange (DF) may be present, this force/torque sensor (FT1), alone, is not configured to sense displacement of such magnitude due to its overly stiff configuration required for admittance control and robotic stability requirements. As a result, measurements from the sensor (DS) adequately capture error conditions such that the control system 30 is made aware of such conditions to subsequently command movement of the manipulator 14 and tool 20 in a stable, predictable, and optimal manner. As will be described below, measurements from the sensor (DS) can be used for various other purposes.

5. Input Device for Tool Control

An input device (ID) is disclosed that can be utilized to receive a user input to control the tool 20 that is coupled to the compliance mechanism 100. The input device (ID) can be located at any suitable location to provide the user with access to control. In one example, as shown, the input device (ID) is coupled to the end effector 22. More specifically, the input device (ID) can be coupled to the body of the tool 20, which is coupled to the moveable portion (MP) of the compliance mechanism 100. In this configuration, the input device (ID) can move along with the moveable portion (MP) during compliant movement.

The input device (ID) can comprise a control lever or digital button, as shown. The input device (ID) may be configured to extend away from the body of the end effector 22 such that it can be easily accessed (e.g., pressed down or lifted up) by one or more fingers or the hand of the user. The input device (ID) can be a moveable, tactile interface. In one implementation, the input device (ID) is moveable in 1DOF, such as the linear direction that is parallel, or coincident, to the tool axis (TA). The input device (ID) can be a joystick, a control knob or dial, an up/down button pair, a slider that is self-centering biased, or the like. The input device (ID) can also be implemented by a digital interface, such as a GUI input on a display device, such as the navigation displays 40,42 or head-mounted device. The input device (ID) can also be located on a pendant that is hand-held and separated from the manipulator 14 or attached by a cable thereto.

An input device sensor (IDS) is configured to detect signals from the input device (ID) responsive to user input. In one specific implementation, as shown in FIGS. 4 and 5, the input device (ID) is a control lever and the input device sensor (IDS) is a force or force/torque sensor (FT2) configured to sense a force or force/torque applied to the input device (ID) by the user. The force/torque sensor (FT2) in one implementation is a 1DOF load cell configured to detect force applied to the input device (ID) in the 1DOF direction as shown in FIG. 3, i.e., linear direction that is parallel, or coincident, to the tool axis (TA). In other instances, the force/torque sensor (FT2) may detect up to 6DOF forces/torques applied to the input device (ID). In another implementation, the input device sensor (IDS) is a displacement sensor configured to measure a displacement of the input device (ID) occurring as a result of user applied force. The displacement measured can be in the 1DOF direction.

The input device sensor (IDS) can be any other suitable type of sensor, such as, but not limited to: a magnetic, electro-magnetic, Hall effect, LVDT, magneto-elastic, magneto-resistive, inductive, capacitive, position encoder, piezo-electric transducer, laser, optical, potentiometer, ultrasonic, inertial, accelerometer, gyroscope, force, strain gauge, image sensor, infrared sensor, or the like. Readings from the input device sensor (IDS) can be transmitted to the tool controller 64, or control system 30.

6. Isolated Manual Mode

With continued reference to FIGS. 4 and 5, the control system 30 may be configured to control movement of the tool 20 with the manipulator 14 in an "isolated" manual mode using the input device (ID) and measurements from the input device sensor (IDS), such as the input device force/torque sensor (FT2). This isolated manual mode is distinguished from the above-described non-isolated manual mode. The phrase "isolated" is used to describe this manual mode because the external forces/torques applied to the tool 20 by the anatomy (A) are mechanically isolated from the input used to control the manipulator 14 in this mode. To further explain, the input device sensor (IDS) is distinguishable from the force/torque sensor (FT1) at the distal flange (DF) of the manipulator 14. Firstly, the input device sensor (IDS) is mechanically isolated from the external forces/torques applied to the tool 20 by the anatomy (A), whereas the manipulator force/torque sensor (FT1) is not mechanically isolated from the external forces/torques applied to the tool 20 by the anatomy (A). When external forces/torques are applied to the tool 20 (e.g., as shown in FIG. 5), the load path (LP) starts from the anatomy (A) and will pass respectively through the tool shaft 25, flexible portion (FP) and stationary portion (SP) until the load path (LP) terminates at the manipulator force/torque sensor (FT1). However, the load path (LP) circumvents the input device sensor (IDS) because the input device sensor (DS) displaces in accordance with the external force/torque. The load readings at the manipulator force/torque sensor (FT1) may be dampened by the operation of the compliance mechanism 100. That is, the compliance mechanism 100 can mechanically filter out error conditions that otherwise would be detected by the manipulator force/torque sensor (FT1). However, the manipulator force/torque sensor (FT1) may still detect forces/torques sufficient to command subsequent motion of the manipulator 14, but in a stable, predictable manner. Nevertheless, the external force at the tool 20 does not impact readings of the input device sensor (IDS) because it is located on the moveable portion (MP) which correspondingly absorbs the displacement caused by the external forces/torques. Unlike the manipulator force/torque sensor (FT1), the input device sensor (IDS) advantageously provides a sensing mechanism that is not impacted by error conditions. The above-described mechanical isolation configuration is particularly useful where the input device sensor (IDS) is implemented as the force/torque sensor (FT2).

Furthermore, when the input device sensor (IDS) is configured as a 1DOF load cell, it advantageously provides a sensing system that is more mechanically constrained than the manipulator force/torque sensor (FT1), which is a 6DOF load cell. This mechanical constraint isolates the user input to the 1DOF direction such that the measurements detected by the input device sensor (ID) accurately represent the user's intentions when controlling the input device (ID). On the other hand, without the input device (ID), the manipulator force/torque sensor (FT1) may detect 6DOF forces/torques that may not accurately represent the user's intentions.

Additionally, any measured forces/torques detected by the input device sensor (IDS) can be computationally "isolated" by being excluded from use in the virtual simulation which determines the next commanded position of the tool 20. In isolated manual mode control, the control system 30 can command the manipulator 14 based on the readings directly obtained from the input device sensor (IDS) without taking into consideration other control forces/torques, such as control forces/torques inputted to the manipulator force-torque sensor (FT1). Isolated manual mode control can be based on a look-up table of force and/or displacement measurements, as obtained by input device sensor (IDS), and corresponding commanded positioning, displacement, or force to command movement of the tool 20. One example of isolated manual mode control will be described below in relation to pedicle screw driving control. As will also be described below, the control system 30 is configured to switch between, or blend, any of the described modes.

a. Screw Thread Pitch Control

With continued reference to FIGS. 4 and 5, one example of using the isolated manual mode can be readily understood with respect to installing pedicle screws (PS) with the tool 20. In this example, the tool 20 is a screw-driver and the pedicle screw (PS) is attached to a distal portion of the shaft 25 for installation to the anatomy (A), such as a vertebral body. The tool 20 is configured to hold the pedicle screw (PS) and to rotate the pedicle screw (PS) about the tool axis (TA). The pedicle screw (PS) may be a self-tapping screw that can be installed without a pilot hole. Alternatively, a pilot hole may be used and with any type of pedicle screw (PS).

In the isolated manual mode, the pedicle screw (PS) can be inserted with assistance of the manipulator 14, whereby the control system 30 controls the insertion such that the rotation speed about the tool axis (TA) and the rate of advancement along the planned trajectory are proportional to the thread geometry of the pedicle screw. Although the isolated manual mode is described in this section, the aspects of thread pitch control can be implemented in the automated mode and non-isolated manual mode.

The thread geometry may include any one or more of pedicle screw (PS) length, thread diameter, depth of thread, head size, and thread pitch. The pedicle screw (PS) geometry can be stored in memory and known to the control system 30. Thread pitch is defined as the number of treads per unit length. In specific example, the pedicle screw (PS) may have a thread pitch of 12 threads per inch. Other exemplary pedicle screws (PS) may have 8, 10, 14, 16 or other number of threads per inch. Having a defined relationship between the manipulator 14 and the pedicle screw (PS), and a known geometry of the pedicle screw (PS) stored in the memory, the control system 30 is configured to ensure to proper rotational speed and advancement speed for inserting a pedicle screw having a particular thread pitch.

The thread geometry of the pedicle screw (PS) can be stored in memory of the robotic system 10 pre-operatively or intraoperatively. In one example, the pedicle screw (PS) is chosen as part of a surgical plan, and the corresponding thread geometry of the pedicle screw (PS) is associated with the pedicle screw (PS) and inputted into the plan. Once the plan is loaded for intraoperative surgery, the robotic system 10 will have the known the thread geometry stored in memory for immediate access. In another example, the operator can manually select different pedicle screws (PS), or can manually input the thread geometry using a GUI affiliated with operation of the system 10. The inputted thread geometry may be obtained from a database stored in memory, or can be derived from the operator obtaining such information from offline specifications associated with a chosen pedicle screw (PS). In any of these examples, the thread geometry can be stored in memory after the operator input using GUI such that the system 10 can subsequently carry out the control techniques described herein with the inputted thread geometry. In yet another example, a measurement tool directly or wirelessly connected to the system 10 may be utilized to scan or measure any intended pedicle screw (PS) to extract the thread geometry and transmit the measured thread geometry to the memory.

The relationship between the pedicle screw thread pitch, the angular, or rotational, position and the depth of insertion, or advancement along the trajectory, is governed by the equation $\theta=D^*(\text{Pitch}/2\pi)$, where $\theta$ is the angular position, D is the depth of insertion in unit length, Pitch is the threads per unit length of the pedicle screw (PS). The control system 30 uses this relationship to control the installation of the pedicle screw. For example, taking the first derivative with request to time, the rate of change in angular position, or rotation speed, $\delta\theta/\delta t$, is equal to the rate of change in depth of insertion, or advancement rate, $\delta D/\delta t$, multiplied by the Pitch divided by $2\pi$. This can be expressed as:

$$\frac{\delta\theta}{\delta t} = \frac{\delta D}{\delta t} * \frac{\text{Pitch}}{2\pi}. \qquad (\text{Eq. 1})$$

In the isolated manual mode, and as shown in FIGS. 4 and 5, the user applies input to the input device (ID). In one implementation, the input device sensor (IDS) is the 1DOF force/torque sensor. The input device sensor (IDS) detects force/torque applied to the input device (ID) in FIG. 4. In FIG. 4, the pedicle screw (PS) is spaced away from the anatomy (A), and therefore, thread pitch control may, or may not, be active as such control is most advantageous during screw insertion. Based on the force/torque applied to the input device (ID) by the user, the control system 30 is configured to control, in the isolated manual mode, the manipulator 14 to linearly displace or advance the tool 20 along the planned trajectory (PT). The linear displacement is dependent on the applied force/torque, and in some cases, can be proportional to the applied force/torque. Assuming thread pitch control is active in the example of FIG. 4, the control system 30 can control the linear displacement and/or the rotation of the tool 20 about the tool axis (TA), whereby the linear displacement and rotational rate are proportional to the known thread geometry stored in the memory.

In FIG. 5, the user either re-applies or continues to apply input to the input device (ID). In this scenario, thread pitch control is active based on the proximity of the pedicle screw (PS) to the anatomy (A). The control system 30, in the isolated manual mode, controls the manipulator 14 based on the input device sensor (IDS) readings. Assuming the sensor reading is a force, the control system 30 controls the linear displacement of the surgical tool to advance the screw (PS) into the anatomy (A) based on the applied force. The linear displacement is dependent on the known thread geometry stored in the memory. If the pedicle screw (PS) is already engaged with the anatomy (A), the control system 30 can also control the rotational rate about the tool axis (TA) knowing that the thread pitch will cause the corresponding displacement. Because the rotational rate and displacement are dependent on the tread pitch, the rotational rate can be used to compute the corresponding displacement, or vice versa. In FIG. 5, external forces/torques are applied to the screw (PS) during engagement with the anatomy (A) in the non-isolated manual mode. As a result, the compliance mechanism 100 may enable the tool 20 to experience a displacement to absorb the contact. The screw (PS) can continue being driven using thread pitch control even while the compliance mechanism 100 provides compliant movement. As the screw (PS) is driven deeper into the anatomy (A), the compliant motion may, or may not, be released depending on the relationship between the anatomy (A), the screw (PS) and the stationary portion (SP) of the compliance mechanism 100. That is, the screw (PS) can be driven using thread pitch control while the compliance mechanism 100 is in the loaded or neutral position. The screw (PS) can be driven to a target depth that can be monitored the control system 30 using kinematic robotic information and/or navigation system 34 tracking data. Once the pedicle screw (PS) is fully implanted, the pedicle screw (PS) can be released from the tool 20. The user can apply force to the input device (ID) (e.g., by pushing up from underneath the control lever) to command the manipulator 14 to move the tool 20 away from the anatomy (A).

Use of thread pitch control advantageously helps to avoid risks of threaded interface between the pedicle screw (PS) and the anatomy (A) causing damage to the bone, the screw (PS), and the surgical tool 20 if the pedicle screw (PS) is inserted incorrectly or improperly. The bone is likely the weakest material and thus most likely to suffer damage if the screw is inserted incorrectly. Improper insertion may occur, for example, when the pedicle screw (PS) advances linearly along the planned trajectory (PT) with insufficient rotation about the tool axis (TA). This may cause bone material to shear off adjacent to the threads and be forced down into the bone. In another example, improper insertion may occur when, for example, the pedicle screw (PS) is rotated about the tool axis (TA) with insufficient displacement along the planned trajectory (PT), causing bone material to shear off adjacent to the threads and be forced back along the threads, in effect over drilling the hole. In either example, the result of the improper insertion is to decrease the strength and amount of bone material to secure the pedicle screw (PS) in the bone.

The compliance mechanism 100, when coupled with thread pitch control, provides additional advantages of ensuring that thread pitch control can be implemented with less risk of errors resulting from forces occurring between the pedicle screw (PS) and the anatomy (A). In other words, even if the screw (PS) is properly commanded according to its thread pitch, there still exists a possibility that the screw (PS) may improperly engage the bone, skive off the bone, strip the bone, not reach the proper depth within the bone, or improperly release from the bone. The compliance mechanism 100 mitigates these risks by absorbing unexpected displacements generally, and more specifically, during thread pitch control.

7. Further Control Examples

Having described the compliance mechanism 100 and the various modes, i.e., automated mode, non-isolated manual mode, and isolated manual mode, described in this section are examples that use the compliance mechanism 100 using various combinations of these modes to facilitate practical surgical workflow.

a. Trajectory Lock

As described above, the control system 30 is configured to control movement of the tool 20 with the manipulator 14 in the automated mode to automatically maintain the tool axis (TA) on the planned trajectory (PT). The control system 30 can maintain this trajectory lock whether the anatomy (A) is stationary or moving based on tracking data from the navigation system 30. However, the trajectory lock in the automated mode can be combined with control in the non-isolated and isolated manual modes. While the tool axis (TA) is automatically maintained on the planned trajectory (PT), the control system 30 can simultaneously control movement of the tool 20 with the manipulator 14 in the non-isolated manual mode to enable the user to command the tool 20 towards or away from the anatomy (A) along the planned trajectory (PT) while the tool 20 is constrained by the planned trajectory (PT). The user commands so by grasping the grip sensor (GS) while simultaneously applying forces/torques that are detected by the manipulator force/torque sensor (FT1).

At any moment during trajectory lock, the control system 30 can switch between manual modes. That is, the isolated manual mode can be switched to the non-isolated manual mode, or vice versa. Assuming control is switched to the isolated manual mode, the tool axis (TA) is automatically maintained on the planned trajectory (PT), and the control system 30 can simultaneously control movement of the tool 20 with the manipulator 14 in the non-isolated manual mode to enable the user to command the tool 20 towards or away from the anatomy (A) along the planned trajectory (PT) while the tool 20 is constrained by the planned trajectory (PT). The user commands so by using the input device (ID).

In either manual mode, the user can use the grip sensor (GS) at any time to release the tool axis (TA) from the planned trajectory (PT) or to bring the tool axis (TA) to the planned trajectory.

b. Condition Detection

The control system 30 is configured to detect a condition and perform an action in response to the condition. The condition may be an error condition or any environmental condition. The response may involve how the control system 30 activates/deactivates or switches between the described modes. The condition can be detected using any described system or component that can obtain data, including the control system 30, the navigation system 34, tool controller 64, manipulator force/torque sensor (FT1), the input device sensor (IDS), the sensor (DS) for the compliance mechanism 100, or any combination thereof. The condition can be a measured value, range of values, threshold value, or the like. The condition can be a measured force, torque, displacement, distance, duration, electrical current, or any combination thereof.

In response to detection of the condition, the control system 30 can perform any of the following: activate or deactivate the isolated manual mode; activate or deactivate the non-isolated manual mode; activate or deactivate the automated mode; switch from the automated mode to the isolated manual mode, or vice-versa; switch from the isolated manual mode to the automated mode, or vice-versa;

switch from the isolated manual mode to the non-isolated manual mode, or vice-versa; combine control using both the automated mode and the isolated manual mode; combine control using both the automated mode and the non-isolated manual mode; combine control using both the non-isolated manual mode and the isolated manual mode, and so on. Other example responses are described below.

The manipulator 14, end effector 22, tool 20, navigation system 34, or any display device may comprise an indicator to inform the user in response to detection of the condition. The indicator could be: visual, e.g., an LED or display device messages, graphics, or animations; haptic or vibratory feedback provided to the manipulator 14 or end effector 22; audible alerts or messages, or any combination thereof. The indicator could describe the condition to the user.

In one example, the manipulator 14 may move the tool 20 to a predefined or threshold distance from the planned trajectory (PT) or move the tool 20 directly to the planned trajectory (PT) using any given mode. Here, the condition is distance of the tool 20 relative to the planned trajectory (PT) and this distance can be determined by the navigation system 34 and optionally using kinematic data from the manipulator 14. In response to detection of the condition, the control system 30 can deactivate the given mode and activate any one or more of the other modes. For instance, the tool 20 can be moved to the planned trajectory (PT) in the automated mode (e.g., as shown in FIG. 11) and then switched to the isolated manual mode (e.g., as shown in FIG. 4) in response to detection of the condition.

In a second example, the manipulator 14 may move the tool 20 along the planned trajectory (PT) towards the anatomy (A) using any given mode until a threshold distance from the anatomy (A) is reached. Here, the condition is the threshold distance of the tool 20 relative to the anatomy (A) and this distance can be determined by the navigation system 34 and optionally using kinematic data from the manipulator 14. In response to detection of the condition, the control system 30 can deactivate the given mode and activate any one or more of the other modes. For instance, the tool 20 can be moved to towards the anatomy (A) in the non-isolated manual mode (e.g., as shown in FIG. 9) and then switched to the isolated manual mode (e.g., as shown in FIG. 5) in response to detection of the condition. The user can then use the input device (ID) to move the tool 20 further towards the anatomy (A) or to manipulate the anatomy (A).

In a third example, such as depicted in FIG. 9, the control system 30 operates in the non-isolated manual mode to enable the user to apply forces/torques to cause the manipulator 14 to move the tool 20 towards the anatomy (A). In the non-isolated manual mode, the tool 20 experiences external forces/torques applied by the anatomy (A). In response to the external forces/torques applied to the tool 20 by the anatomy, the compliance mechanism 100 enables the tool 20 to move relative to the manipulator 14 such that the moveable portion (MP) experiences a displacement relative to the stationary portion (SP). The sensor (DS) of the compliance mechanism 100 is configured to measure the displacement of the moveable portion (MP) relative to the stationary portion (SP). The control system 30 is configured to evaluate the displacement measured by the sensor (DS) relative to a threshold. The threshold can be a threshold displacement, a threshold duration of displacement, or both. The threshold duration of displacement can be understood as the period of time during which any displacement is detected, or during which the threshold displacement is detected. In one example, the threshold displacement is greater than 1 mm and the threshold duration is greater than 1 second. In this example, the threshold is indicative of the condition being that the tool 20 is improperly or inadvertently engaging or contacting the anatomy (A) in the non-isolated manual mode. The control system 30 determines that the displacement measured by the sensor (DS) exceeds the threshold. Since this threshold is indicative of an error and because the manipulator 14 is being controlled in the non-isolated manual mode, the control system 30 performs an error mitigation action. The control system 30 is configured to do one or more of the following: constrain movement of the manipulator 14 in the non-isolated manual mode to prevent the user from further moving the tool 20, e.g., towards the anatomy (A); deactivate the non-isolated manual mode; activate the isolated manual mode; control the manipulator 14 (e.g., in the automated mode) to move the tool 20 away from the anatomy (A); disable operation of the manipulator 14; and generate an alert or indicator for the user. If the control system 30 determines that the displacement measured by the sensor (DS) does not exceed, or no longer exceeds, the threshold, the control system 30 can permit or resume movement of the manipulator 14 in the non-isolated manual mode to enable the user to move the tool 20 towards the anatomy (A).

In a fourth example, such as depicted in FIG. 5, the control system 30 controls movement of the tool 20 with the manipulator 14 in the isolated manual mode to enable the user to use the input device (ID) to move the tool 14 to engage the anatomy (A) along the planned trajectory (PT) while the tool 20 is constrained by the planned trajectory (PT). This movement could be with or without thread pitch control. During this movement, the tool 20 experiences external forces/torques applied by the anatomy (A). In response to the external forces/torques applied to the tool 20 by the anatomy (A), the compliance mechanism 100 enables the tool 20 to move relative to the manipulator 14 such that the moveable portion (MP) experiences a displacement relative to the stationary portion (SP). The sensor (DS) of the compliance mechanism 100 is configured to measure the displacement of the moveable portion (MP) relative to the stationary portion (SP). The control system 30 can evaluate the displacement measured by the sensor (DS) relative to a threshold. In this example, the threshold is indicative of the condition being that the tool 20 and/or pedicle screw (PS) is engaging or contacting the anatomy (A) in the isolated manual mode. However, unlike the third example above, this contact may not necessarily be an error condition due to the isolated nature of this manual mode. Hence, the threshold of this example may comprise greater allowable values of displacement and/or duration of displacement. In one example, for the isolated manual mode, the threshold displacement can be greater than 3 mm and the threshold duration can be greater than 10 second. The control system 30 can determine if an error condition is present if the threshold is exceeded. If the control system 30 determines that this is an error condition, the control system 30 is configured to do one or more of the following: constrain movement of the manipulator 14 in the isolated manual mode to prevent the user from further moving the tool 20, e.g., towards the anatomy (A) along the planned trajectory (PT); deactivate the isolated manual mode; activate the non-isolated manual mode; control the manipulator 14 (e.g., in the automated mode) to move the tool 20 off the planned trajectory (PT) and/or away from the anatomy (A); disable operation of the manipulator 14; and generate an alert or indicator for the user. If the control system 30 determines that this is not an error condition, the control system 30 is configured to do one or more of the following: permit or resume movement of the manipulator 14 in the isolated manual mode to enable the user to continue moving the tool 20, e.g., towards the anatomy (A) along the planned trajectory (PT); update the target depth of the tool 20 or pedicle screw (PS); and generate an alert or indicator for the user.

In a fifth example, thread pitch control is utilized by the manipulator 14, whereby the tool 20 holds the pedicle screw (PS) and the manipulator 14 controls the linear displacement and/or rotational rate of the tool 20 to drive the pedicle screw (PS), and optionally along the planned trajectory (PT). The linear displacement and/or rotational rate are each proportional to the known thread geometry of the pedicle screw (PS) stored in the memory. This driving can occur in any one or more of the above-described modes, e.g., non-isolated manual, isolated manual, or automated mode. During or after advancement of the pedicle screw (PS) towards the anatomy (A) by the manipulator 14, the sensor (DS) can detect from the compliance mechanism 100 a condition whereby the tool 20 has experienced the displacement relative to the manipulator 14. This condition is indicative of a situation wherein the pedicle screw (PS)_may be improperly engaging the anatomy (A). In response, the control system 30 is configured to do one or more of the following: constrain movement of the manipulator 14 to prevent the user from further moving the tool 20, e.g., towards the anatomy (A) along the planned trajectory (PT); deactivate the currently active mode; activate another mode; control the manipulator 14 (e.g., in the automated mode) to move the tool 20 off the planned trajectory (PT) and/or away from the anatomy (A); disable operation of the manipulator 14; and generate an alert or indicator for the user. Any of the techniques described in this section can be implemented with any of the described features from the previous sections.

c. Error Detection Using Navigation Tracking Data

In one example, the navigation system 34 tracks the anatomy (A) and generates tracking data related to pose of the anatomy (A). Meanwhile, thread pitch control is utilized by the manipulator 14 to advance the pedicle screw (PS) according to a commanded displacement that is proportional to the known thread geometry of the pedicle screw (PS) stored in the memory. The commanded displacement can alternatively or additionally be based on controlling the rotational rate of the tool 20, whereby the rotational rate is proportional to the known thread geometry of the pedicle screw (PS) stored in the memory. The displacement can be commanded in any one or more of the above-described modes, e.g., non-isolated manual, isolated manual, or automated mode. For example, the displacement can be commanded in an automated manner or based on user input. In this example, the control system 30 evaluates the tracking data from the navigation system 34 and the commanded displacement of the screw (PS). If the screw (PS) properly engaged and entered the anatomy (A), then anatomy (A) should remain substantially stationary. If the screw (PS) improperly engaged or did not enter the anatomy (A), then anatomy (A) may be moved due to contact forces applied by the screw (PS). The control system 30 can determine from the tracking data whether or not the anatomy (A) moved during or after driving of the screw (PS), and if so, the control system 30 can further determine the displacement of anatomy movement. The control system 30 can compare the commanded screw displacement value with the tracking data to detect an error related to engagement between the screw (PS) and the anatomy (A). In one example, the control system 30 determines that commanded screw displacement value is greater than the anatomy displacement value to conclude that an error did not occur. In another example, the control system 30 determines that commanded screw displacement value is equal to, or less than, the anatomy displacement value to conclude that an error occurred. In other words, the anatomy (A) was displaced by the screw (A) not properly engaging the anatomy (A) during or after the commanded displacement. The above-described technique can optionally be performed using the displacement threshold(s) described above. In other words, the control system 30 can further evaluate the displacement of the anatomy (A) or screw (PS) relative to a threshold displacement and/or duration of displacement to make determinations about whether an error occurred or not.

In another example, the navigation system 34 tracks the state of the TCP of the tool 20 using tracking data, e.g., data from tracking devices or elements coupled to the manipulator 14, end effector 22 and/or tool 20. Meanwhile, the tool 20 may experience a displacement causing the tool 20 to move relative to the manipulator 14 through motion provided by the compliance mechanism 100. During or after such displacement, the navigation system 34 can track the displaced state of the TCP. The control system 30 can obtain measurements from the sensor (DS) that measures the displacement of the tool 20 relative to the manipulator 14. The control system 30 can compute the displaced state of the TCP by combining kinematic data of the manipulator 14 with the measured displacement from the sensor (DS). Thereafter, the control system 30 can compare the displaced state of the TCP obtained by tracking data with the displaced state of the TCP obtained by kinematic and sensor (DS) measurement data. If the displaced states correspond to each other, then the control system 30 can determine that the tracking data and/or sensor (DS) data are accurate or that the compliance mechanism 100 is properly operating. If the displaced states do not correspond to each other, then the control system 30 can determine an error, e.g., that the tracking data is inaccurate, the sensor (DS) data is inaccurate, and/or the compliance mechanism 100 is improperly operating. These techniques can be implemented with any of the described features from the previous sections.

d. Control Based on Displacement of Tool

In some scenarios, it may be practical to control manipulator 14 based on the measure of the displacement of the tool 20 relative to the manipulator 14, where the compliant motion of tool 20 is provided by the compliance mechanism 100 and the displacement is detected by the sensor (DS) of the compliance mechanism 100. Here, the control system 30 can perform any one or more of the following actions to control the manipulator 14 based on the measured displacement: advance or retract the tool 20 based on the measured displacement; change the advancement rate for thread pitch control based on the measured displacement; change the rotational rate for thread pitch control based on the measured displacement; move the manipulator 14 to reduce the displacement, e.g., to move the compliance mechanism 100 to the neutral position; move the manipulator 14 to maintain a predetermined relationship between the tool 20 and the anatomy (A) based on the measured displacement, or the like. The amount the manipulator 14 is moved can be proportional to the measured displacement or otherwise correlated to the measured displacement. These techniques can be implemented with any of the described features from the previous sections.

e. Flexible Portion as Force/Torque Sensor

As described above, the flexible portion (FP) helps facilitate operation of the compliance mechanism 100. In some scenarios, it may be practical to further use the flexible portion (FP) for sensing load applied to the tool 20. A force/torque sensor or load cell can be coupled to the flexible portion (FP) to detect deformation of the flexible portion (FP). Once the flexible portion (FP) biases during compliant motion, the flexible portion (FP) sensor can determine forces/torques applied to the tool 20. In one example, the flexible portion (FP) sensor is a 1DOF load cell for detecting force parallel, or coincident, to the tool axis (TA). This flexible portion (FP) sensor may be utilized instead of, or in addition to, the sensor (DS) or manipulator force/torque sensor (FT1). The flexible portion (FP) sensor can be utilized for any of the above-described modes. These techniques can be implemented with any of the described features from the previous sections.

f. Anatomical Feature Detection

Anatomical features may be naturally present or manually formed from, or in, the anatomy (A) for surgery. These anatomical features, in one example, are natural surfaces or resected surfaces of a bone. For instance, the anatomical feature may be a spinous process or pedicle. In another example, the anatomical features are holes formed in the anatomy (A). The holes could also be peg holes for receiving a tibial or femoral implant. The holes may be pilot holes in a vertebral body in preparation for pedicle screw (PS) implantation. The holes may be formed using the manipulator 14 or using a separate hand-held drill controlled by the operator.

In some scenarios, the system 10 may be unaware of the location of the anatomical feature. However, robotic control may be adversely affected by an anatomical feature that is unknown to the system 10 or not accurately localized by the system 10. Accordingly, the system 10 can utilize the manipulator 14 and tool 20 to detect the location of any anatomical features. In one example, the manipulator 14 moves the tool 20 across the surface of the anatomy (A) and measures sensor readings during this operation. This may be done using any of the above-described modes. In one instance, the readings are obtained from the manipulator force/torque sensor (FT1). Additionally, or alternatively, the readings are obtained from the sensor (DS) of the compliance mechanism 100. Additionally, or alternatively, the readings are obtained from the flexible portion (FP) sensor. The sensor readings can be force, torque, pressure, displacement, or the like. The control system 30 can log coordinates of the TCP during surface scanning. Peaks and valleys may be recorded by the control system 30 to map out features of the anatomy (A), such as a hole. The coordinates can be compared or combined with navigation data. The virtual anatomical model can also be utilized to import coordinate data therein or cross-check coordinate data. Certain types of anatomical features may have predefined geometry, or force and/or displacement profiles that could be stored in memory and compared with the TCP coordinates obtained during surface scanning. If the TCP coordinates match a specific profile or geometry, the control system 30 can determine the identify, geometry and coordinate of the anatomical feature. Thereafter, the control system 30 may be use this information to register the anatomical feature with the navigation system 34 so that the anatomical feature can be visualized on a display and used for intraoperative surgical planning and navigation purposes. These techniques can be implemented with any of the described features from the previous sections.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system comprising:
a robotic manipulator;
an end effector supported by the robotic manipulator, the end effector comprising:
   a surgical tool configured to interact with an anatomy; and
   a compliance mechanism configured to enable the surgical tool to move relative to the robotic manipulator in response to external forces/torques applied to the surgical tool by the anatomy, the compliance mechanism comprising a stationary portion coupled to the robotic manipulator, a moveable portion coupled to the surgical tool, and a flexible portion disposed between the stationary portion and the moveable portion; and
an input device comprising a first force/torque sensor configured to sense a force/torque applied to the input device by a user, wherein the first force/torque sensor is a one degree-of-freedom (1DOF) load cell and is mechanically isolated from the external forces/torques applied to the surgical tool; and
a control system configured to control 1DOF movement of the surgical tool with the robotic manipulator in an isolated manual mode in which the robotic manipulator is commanded based on the force/torque applied to the input device by the user, the applied force/torque being sensed by the first force/torque sensor.

2. The surgical system of claim 1, wherein:
the surgical tool is configured to hold a screw and to rotate the screw about a rotational axis, the screw having a known thread geometry; and
the control system comprises a memory for storing the known thread geometry, and based on the force/torque applied to the input device by the user, the control system is configured to control, in the isolated manual mode, a rotational rate of the surgical tool to rotate the screw about the rotational axis and/or to control a linear displacement of the surgical tool to advance the screw, wherein the rotational rate and the linear displacement of the surgical tool are each proportional to the known thread geometry stored in the memory.

3. The surgical system of claim 1, comprising a second force/torque sensor coupled between the robotic manipulator and the end effector, the second force/torque sensor configured to sense external forces/torques applied to the end effector or the surgical tool by the user or by the anatomy.

4. The surgical system of claim 3, wherein the control system is configured to control movement of the surgical tool with the robotic manipulator in a non-isolated manual mode in which the robotic manipulator is commanded based on external forces/torques applied to the end effector or the surgical tool by the user, the external forces/torques being sensed by the second force/torque sensor.

5. The surgical system of claim 4, wherein the control system is configured to:
define virtual constraints on movement of the surgical tool;
simulate dynamics of the surgical tool in a virtual simulation based on the virtual constraints and the external forces/torques being sensed by the second force/torque sensor; and control movement of the surgical tool with the robotic manipulator based on the virtual simulation; and wherein the force/torque sensed by the first force/torque sensor is excluded from the virtual simulation.

6. The surgical system of claim 4, wherein:

the second force/torque sensor is a 6DOF load cell; and the control system is configured to control movement of the surgical tool in at least 1DOF with the robotic manipulator in the non-isolated manual mode.

7. The surgical system of claim 4, wherein the control system is configured to detect a condition, and in response to detection of the condition:

activate the isolated manual mode and deactivate the non-isolated manual mode;

deactivate the isolated manual mode and activate the non-isolated manual mode; or combine control using both the isolated manual mode and the non-isolated manual mode.

8. The surgical system of claim 7, comprising:

a navigation system configured to track a distance between the surgical tool and the anatomy; and the control system being coupled to the navigation system and being configured to:

deactivate the isolated manual mode and activate the non-isolated manual mode;

control movement of the surgical tool with the robotic manipulator in the non-isolated manual mode to enable the user to move the surgical tool towards the anatomy;

detect the condition being the distance between the surgical tool and the anatomy satisfying a threshold distance during control in the non-isolated manual mode;

in response to detection of the condition, deactivate the non-isolated manual mode and activate the isolated manual mode; and control movement of the surgical tool with the robotic manipulator in the isolated manual mode to enable the user to move the surgical tool towards the anatomy.

9. The surgical system of claim 4, wherein:

the surgical tool comprises a tool axis;

a navigation system is configured to track the anatomy and register a planned trajectory to the anatomy; and the control system being is coupled to the navigation system and is configured to:

control movement of the surgical tool with the robotic manipulator in the isolated manual mode to enable the user to move the surgical tool towards the anatomy along the planned trajectory while the surgical tool is constrained by the planned trajectory; and/or control movement of the surgical tool with the robotic manipulator in the non-isolated manual mode to enable the user to (1) move the surgical tool from a first position off the planned trajectory to a second position on the planned trajectory; and/or (2) move the surgical tool towards the anatomy along the planned trajectory while the surgical tool is constrained by the planned trajectory.

10. The surgical system of claim 9, wherein:

the control system is configured to control movement of the surgical tool with the robotic manipulator in the non-isolated manual mode to enable the user to move the surgical tool to engage the anatomy along the planned trajectory while the surgical tool is constrained by the planned trajectory, in the non-isolated manual mode, the surgical tool experiences external forces/torques applied by the anatomy;

in response to the external forces/torques applied to the surgical tool by the anatomy, the moveable portion is configured to experience a displacement relative to the stationary portion;

a sensor is configured to measure the displacement of the moveable portion relative to the stationary portion; and the control system is configured to evaluate the displacement measured by the sensor.

11. The surgical system of claim 10, wherein the control system is configured to evaluate the displacement measured by the sensor relative to a threshold, the threshold being one or both of: a threshold displacement and a threshold duration of the displacement.

12. The surgical system of claim 11, wherein the control system determines that the displacement measured by the sensor exceeds the threshold, and in response, the control system is configured to perform one or more of the following:

constrain movement of the robotic manipulator in the non-isolated manual mode to prevent the user from moving the surgical tool towards the anatomy along the planned trajectory;

deactivate the non-isolated manual mode;

activate the isolated manual mode;

control the robotic manipulator to move the surgical tool off the planned trajectory; and disable operation of the robotic manipulator.

13. The surgical system of claim 11, wherein the control system determines that the displacement measured by the sensor does not exceed the threshold, and in response, the control system is configured to permit or resume movement of the robotic manipulator in the non-isolated manual mode to enable the user to move the surgical tool towards the anatomy along the planned trajectory.

14. The surgical system of claim 9, wherein:

the control system is configured to control movement of the surgical tool with the robotic manipulator in the isolated manual mode to enable the user to move the surgical tool to engage the anatomy along the planned trajectory while the surgical tool is constrained by the planned trajectory, in the isolated manual mode, the surgical tool experiences external forces/torques applied by the anatomy;

in response to the external forces/torques applied to the surgical tool by the anatomy, the moveable portion is configured to experience a displacement relative to the stationary portion;

a sensor is configured to measure the displacement of the moveable portion relative to the stationary portion; and the control system is configured control the robotic manipulator based on the displacement measured by the sensor.

15. The surgical system of claim 9, wherein the control system is configured to control movement of the surgical tool with the robotic manipulator in an automated mode to automatically maintain the tool axis on the planned trajectory.

16. The surgical system of claim 15, wherein the control system is configured to control movement of the surgical tool with the robotic manipulator in the automated mode to automatically move the surgical tool from a first position off the planned trajectory to a second position on the planned trajectory.

17. The surgical system of claim 15, wherein the control system is configured to:

control movement of the surgical tool with the robotic manipulator in the automated mode to automatically maintain the tool axis on the planned trajectory, and simultaneously:

control movement of the surgical tool with the robotic manipulator in the isolated manual mode to enable the user to move the surgical tool towards the anatomy along the planned trajectory while the surgical tool is constrained by the planned trajectory; and/or control movement of the surgical tool with the robotic manipulator in the non-isolated manual mode to enable the user to move the surgical tool towards the anatomy along the planned trajectory while the surgical tool is constrained by the planned trajectory.

18. The surgical system of claim 1, wherein:

the surgical tool comprises a tool axis; and in response to external forces/torques applied to the surgical tool by the anatomy, the compliance mechanism enables the surgical tool to move relative to the robotic manipulator in an axial direction that is parallel to, or coincident with, the tool axis.

19. The surgical system of claim 1, wherein the compliance mechanism is configured such that the moveable portion:

is in a neutral position in an absence of external forces/torques applied to the surgical tool;

is in a loaded position as external forces/torques are applied to the surgical tool; and returns to the neutral position in response to external forces/torques no longer being applied to the surgical tool.

20. The surgical system of claim 1, wherein:

the surgical tool comprises a tool axis;

the stationary portion comprises an upper platform and a lower platform and a rail extending between the upper platform and the lower platform and the rail being oriented in a direction that is parallel to, or coincident with, the tool axis;

the moveable portion comprises a body with an upper surface and a lower surface and the body defines a channel that extends from the upper surface to the lower surface and the rail is disposed through the channel, and the moveable portion is configured to slide along the rail between the upper platform and lower platform of the stationary portion and slide in a direction parallel to, or coincident with, the tool axis; and the flexible portion comprises a biasing device that is disposed between the upper platform and the upper surface or disposed between the lower platform and the lower surface.

21. The surgical system of claim 1, wherein:

the robotic manipulator comprises a robotic arm including a plurality of links and joints, and wherein the end effector is coupled to the robot arm; or wherein the robotic manipulator is hand-held such that a user supports the robotic manipulator against a force of gravity, the robotic manipulator comprising a grasping portion configured to be grasped by the user, and an actuatable portion that is configured to move relative to the grasping portion, wherein the end effector is coupled to the actuatable portion.

22. An end effector for a surgical system, the end effector being configured to be supported by a robotic manipulator that is operated by a control system, the end effector comprising:

a surgical tool;

a compliance mechanism configured to enable the surgical tool to move relative to the robotic manipulator in response to external forces/torques applied to the surgical tool, the compliance mechanism comprising a stationary portion configured to couple to the robotic manipulator, a moveable portion coupled to the surgical tool, and a flexible portion disposed between the stationary portion and the moveable portion; and an input device comprising a first force/torque sensor configured to sense a force/torque applied to the input device by a user, wherein the first force/torque sensor is a one degree-of-freedom (1DOF) load cell and is mechanically isolated from the external forces/torques applied to the surgical tool, wherein the input device is configured to provide one or more signals to the control system to control 1DOF movement of the surgical tool with the robotic manipulator in an isolated manual mode, the one or more signals being generated based on the force/torque applied to the input device by the user, the applied force/torque being sensed by the first force/torque sensor.

23. A surgical system comprising:

a robotic manipulator;

a surgical tool supported by the robotic manipulator;

a compliance mechanism configured to enable the surgical tool to move relative to the robotic manipulator in response to external forces/torques applied to the surgical tool, the compliance mechanism comprising a stationary portion coupled to the robotic manipulator, a moveable portion coupled to the surgical tool, and a flexible portion disposed between the stationary portion and the moveable portion; and an input device comprising a first force/torque sensor configured to sense a force/torque applied to the input device by a user, wherein the first force/torque sensor is a one degree-of-freedom (1DOF) load cell and is mechanically isolated from the external forces/torques applied to the surgical tool; and a control system configured to control 1DOF movement of the surgical tool with the robotic manipulator in an isolated manual mode in which the robotic manipulator is commanded based on the force/torque applied to the input device by the user, the applied force/torque being sensed by the first force/torque sensor.

* * * * *